US007455837B2

(12) United States Patent
Guo et al.

(10) Patent No.: US 7,455,837 B2
(45) Date of Patent: Nov. 25, 2008

(54) COMPOSITIONS AND METHODS FOR THE DIAGNOSIS AND TREATMENT OF SEPSIS

(75) Inventors: Renfeng Guo, Ann Arbor, MI (US); Niels C. Riedemann, Hannover (DE); Peter A. Ward, Ann Arbor, MI (US); Markus Huber-Lang, Blaustein-Arnegg (DE); J. Vidya Sarma, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 616 days.

(21) Appl. No.: 10/701,871

(22) Filed: Nov. 5, 2003

(65) Prior Publication Data

US 2004/0166541 A1    Aug. 26, 2004

Related U.S. Application Data

(60) Provisional application No. 60/423,759, filed on Nov. 5, 2002.

(51) Int. Cl.
*A61K 39/395* (2006.01)
*A61K 39/00* (2006.01)
*A61K 38/16* (2006.01)

(52) U.S. Cl. ............ 424/143.1; 424/139.1; 514/8; 514/921

(58) Field of Classification Search ............ 424/139.1, 424/143.1; 514/8, 921, 2; 530/388.25, 389.3, 530/387.9
See application file for complete search history.

(56) References Cited

U.S. PATENT DOCUMENTS

| 5,480,974 | A | 1/1996 | Morgan et al. | |
| 5,573,921 | A * | 11/1996 | Behnke et al. | 435/7.92 |
| 6,866,845 | B1 * | 3/2005 | Ward et al. | 424/139.1 |
| 2005/0244406 | A1 | 11/2005 | MacKay | |

FOREIGN PATENT DOCUMENTS

EP    0 245 993    * 11/1987

OTHER PUBLICATIONS

Huber-Lang et al. The Faseb J. 16: 1567-1574, Oct. 2002.*
Werfel et al. J. Immunol. 157: 1729-1735, 1996.*
Rothermel et al. Scand. J. Immunol. 52: 401-410, 2000.*
Read et al. J. Exp. Med. 182: 267-272, 1995.*
Hollenberg et al. Am. J. Respir. Crit. Care Med. 164: 891-895, Sep. 2001.*
Deitch EA. Shock 24: Suppl. 1, 19-23, 2005.*
Hyde et al. Infect. Immun. 58: 519-624, 1990.*
Hotchkiss et al. PNAS 96: 14541-14546, 1999.*
Mandecki et al., "Chemical synthesis of a gene encoding the human complement fragment C5a and its expression in *Escherichia*," PNAS U S A. Jun.;82(11):3543 7(1985).
Reidemann et al., "Increased C5a receptor expression in sepsis," (2002) J. Clin. Invest. 110:101-108.
Solomkin et al., "Neutrophil dysfunction in sepsis. II. Evidence for the role of complement activation products in cellular deactivation," Surgery 90:319-327, (1981).
Van Epps, et al., "Relationship of C5a receptor modulation to the functional responsiveness of human polymorphonuclear leukocytes to C5a," J. Immunol. 150:246-252 (1993).
Ward and Becker, "The deactivation of rabbit neutrophils by chemotactic factor and the nature of the activatable esterase," J. Exp. Med. 127:693-709 (1968).
Olson et al., "The role of C5 in septic lung injury," Ann. Surg. 202:771-776 (1985).
Wong et al., "Small molecular probes for G-protein-coupled C5a receptors: conformationally constrained antagonists derived from the C terminus of the human plasma protein C5a," (1998) J. Med. Chem. 41,3417-3425.
Mollison et al., (1992) FASEB J. 6,A2058.
Drapeau et al., "Synthetic C5a receptor agonists. Pharmacology, metabolism and in vivo cardiovascular and hematologic effects," (1993) Biochem. Pharmacol. 45,1289-1299.
Konteatis et al., "Development of C5a receptor antagonists. Differential loss of functional responses," (1994) J. Immunol. 153,4200-4205.
Woodruff et al., "Species dependence for binding of small molecule agonist and antagonists to the C5a receptor on polymorphonuclear leukocytes," Inflammation 25, 171-7. (2001).
Haynes et al., "Inhibition of C5a-induced neutrophil chemotaxis and macrophage cytokine production in vitro by a new C5a receptor antagonist," Biochem Pharmacol 60, 729-33. (2000).
Strachan et al., "A new small molecule C5a receptor antagonist inhibits the reverse-passive Arthus reaction and endotoxic shock in rats," J Immunol 164, 6560-5. (2000).
Paczkowski et al., "Pharmacological characterization of antagonists of the C5a receptor," Br J Pharmacol 128, 1461-6 (1999).
Finch et al., J Med Chem 42, 1965-74. (1999).
Strachan et al., "Inhibition of immune-complex mediated dermal inflammation in rats following either oral or topical administration of a small molecule C5a receptor antagonist," Br J Pharmacol 134, 1778-86. (2001).
Short et al., "Effects of a new C5a receptor antagonist on C5a- and endotoxin-induced neutropenia in the rat," (1999) Br. J. Pharmacol. 126,551-554.
Mulligan et al., "Requirement and role of C5a in acute lung inflammatory injury in rats," (1996) J. Clin. Invest. 98,503-512.
Larsen et al., "The pulmonary response of C5 sufficient and deficient mice to immune complexes," (1981) Am. Rev. Respir. Dis. 123,434-439.
Koch et al., (1997) Shock 7,42-48.
Short et al., "Response-selective C5a agonists: differential effects on neutropenia and hypotension in the rat," (1999) Br. J. Pharmacol. 128,511-514.
Goya et al., "Immunologic assessment of host defense impairment in patients with septic multiple organ failure: relationship between complement activation and changes in neutrophil function," (1994) Surgery 115,145-155.
Hecke et al., "Circulating complement proteins in multiple trauma patients—correlation with injury severity, development of sepsis, and outcome," (1997) Crit. Care Med. 25,2015-2024.
Czermak et al., "Protective effects of C5a blockade in sepsis," (1999) Nature Med.. 5,788-792.

* cited by examiner

*Primary Examiner*—S. Devi
(74) *Attorney, Agent, or Firm*—Casmier Jones, S.C.

(57) ABSTRACT

The present invention relates to methods and compositions for the diagnosis and treatment of sepsis. The present invention also provides methods of providing a prognosis to a patient with sepsis. In particular, the present invention relates to compositions and methods for the detection of C5aR expression and the correlation of C5aR expression level with prognosis in sepsis.

2 Claims, 12 Drawing Sheets

Time course of C5aR expression on neutrophils after CLP

Correlation of C5aR expression on neutrophils with survival

Effect of C5a Receptor Antagonist (C5aRa) on Survival in CLP induced Sepsis in Mice

Effect of anti-C5aR Antibody Treatment (20μg/animal) on Survival in CLP-induced Sepsis in Mice

SEQUENCE LISTING

<160> NUMBER OF SEQ ID NOS: 2

<210> SEQ ID NO 1
<211> LENGTH: 36
<212> TYPE: DNA
<213> ORGANISM: Artificial Sequence
<220> FEATURE:
<223> OTHER INFORMATION: Synthetic

<400> SEQUENCE: 1
gtgtcgcgag tcagccatat gaacctgcat ctccta        36

<210> SEQ ID NO 2
<211> LENGTH: 39
<212> TYPE: DNA
<213> ORGANISM: Artificial Sequence
<220> FEATURE:
<223> OTHER INFORMATION: Synthetic

<400> SEQUENCE: 2
gtcacatcgc gacacggatc ctcaccttcc cagttggac        39

COMPOSITIONS AND METHODS FOR THE DIAGNOSIS AND TREATMENT OF SEPSIS

This application claims priority to provisional patent application Ser. No. 60/423,759, filed Nov. 5, 2002, which is herein incorporated by reference in its entirety.

This invention was made with Government support under the National Institutes of Health (NIH) awarded by contracts GM61656-01, GM-29507, and HL-31963. The government may have certain rights in this invention.

FIELD OF THE INVENTION

The present invention relates to methods and compositions for the diagnosis and treatment of sepsis. The present invention also provides methods of providing a prognosis to a patient with sepsis. In particular, the present invention relates to compositions and methods for the detection of C5aR expression and the correlation of C5aR expression level with prognosis in sepsis.

BACKGROUND OF THE INVENTION

Sepsis is a major cause of morbidity and mortality in humans and other animals. It is estimated that 400,000-500,000 episodes of sepsis resulted in 100,000-175,000 human deaths in the U.S. alone in 1991. Sepsis has become the leading cause of death in intensive care units among patients with non-traumatic illnesses (Machiedo et al., *Surg. Gyn. & Obstet.* 152:757-759 (1981)). It is also the leading cause of death in young livestock, affecting 7.5-29% of neonatal calves (Morris et al., *Am. J. Vet. Res.* 47:2554-2565 (1986)), and is a common medical problem in neonatal foals (Hoffman et al., *J. Vet. Int. Med.* 6:89-95 (1992)). Despite the major advances of the past several decades in the treatment of serious infections, the incidence and mortality due to sepsis continues to rise (Wolff, *New Eng. J. Med.* 324:486-488 (1991)).

Sepsis is a systemic reaction characterized by arterial hypotension, metabolic acidosis, decreased systemic vascular resistance, tachypnea and organ dysfunction. Sepsis can result from septicemia (i.e., organisms, their metabolic end-products or toxins in the blood stream), including bacteremia (i.e., bacteria in the blood), as well as toxemia (i.e., toxins in the blood), including endotoxemia (i.e., endotoxin in the blood). The term "bacteremia" includes occult bacteremia observed in young febrile children with no apparent foci of infection. The term "sepsis" also encompasses fungemia (i.e., fungi in the blood), viremia (i.e., viruses or virus particles in the blood), and parasitemia (i.e., helminthic or protozoan parasites in the blood). Thus, septicemia and septic shock (acute circulatory failure resulting from septicemia often associated with multiple organ failure and a high mortality rate) may be caused by a number of organisms.

The systemic invasion of microorganisms presents two distinct problems. First, the growth of the microorganisms can directly damage tissues, organs, and vascular function. Second, toxic components of the microorganisms can lead to rapid systemic inflammatory responses that can quickly damage vital organs and lead to circulatory collapse (i.e., septic shock) and oftentimes, death.

There are three major types of sepsis characterized by the type of infecting organism. Gram-negative sepsis is the most common and has a case fatality rate of about 35%. The majority of these infections are caused by *Escherichia coli, Klebsiella pneumoniae* and *Pseudomonas aeruginosa*. Gram-positive pathogens such as the Staphylococci and Streptococci are the second major cause of sepsis. The third major group includes fungi, with fungal infections causing a relatively small percentage of sepsis cases, but with a high mortality rate.

Many of these infections are acquired in a hospital setting and can result from certain types of surgery (e.g., abdominal procedures), immune suppression due to cancer or transplantation therapy, immune deficiency diseases, and exposure through intravenous catheters. Sepsis is also commonly caused by trauma, difficult newborn deliveries, and intestinal torsion (especially in dogs and horses).

Many patients with septicemia or suspected septicemia exhibit a rapid decline over a 24-48 hour period. Thus, rapid methods of diagnosis and treatment delivery are essential for effective patient care. Unfortunately, a confirmed diagnosis as to the type of infection traditionally requires microbiological analysis involving inoculation of blood cultures, incubation for 18-24 hours, plating the causative organism on solid media, another incubation period, and final identification 1-2 days later. Therefore, therapy must be initiated without any knowledge of the type and species of the pathogen, and with no means of knowing the extent of the infection. Clearly, there is a great need for agents capable of diagnosing and treating sepsis.

SUMMARY OF THE INVENTION

The present invention relates to methods and compositions for the diagnosis and treatment of sepsis. The present invention also provides methods of providing a prognosis to a patient with sepsis. In particular, the present invention relates to compositions and methods for the detection of C5aR expression and the correlation of C5aR expression level with prognosis in sepsis.

Accordingly, in some embodiments, the present invention provides a method of determining a prognosis, comprising providing a blood sample from a subject, wherein the blood sample comprises white blood cells (e.g., neutrophils), and wherein the subject is diagnosed with sepsis; and detecting the level of expression of C5aR on the white blood cells (e.g., neutrophils). In some embodiments, an increased level of expression of the C5aR on the neutrophils relative to a normal standard is indicative of an increased rate of survival of the subject. In other embodiments, a decreased level of expression of the C5aR on the neutrophils relative to a normal standard is indicative of a decreased rate of survival of the subject. In some embodiments, detecting the level of expression of C5aR on the neutrophils comprises exposing the blood sample to an anti-C5aR antibody. In some embodiments, the antibody is labeled (e.g., with a fluorescent label). In some embodiments, detecting the level of expression of C5aR on the neutrophils further comprises subjecting the blood sample to fluorescence activated cell sorting.

The present invention further provides a method of screening compounds, comprising providing a neutrophil, wherein the neutrophil expresses C5aR; and one or more test compounds; and contacting the neutrophil with the test compound; and detecting the level at which the neutrophil expresses the C5aR. In some embodiments, the neutrophil expresses more of the C5aR in the presence of the test compound than in the absence of the test compound. In some embodiments, detecting the level of expression of C5aR on the neutrophils comprises exposing the blood sample to an anti-C5aR antibody. In some embodiments, the antibody is labeled (e.g., with a fluorescent label). In certain embodiments, detecting the level of expression of C5aR on the neutrophils further comprises subjecting the blood sample to fluorescence activated cell sorting. In some embodiments, the cell is in a host. In certain embodiments, the host has been diagnosed with sepsis. In some embodiments, the host is a non-human animal (e.g., an animal model of sepsis). In some embodiments, the test compound is an anti-C5aR antibody.

The present invention additionally provides a kit for providing a prognosis to a subject diagnosed with sepsis, comprising a reagent for determining the level of C5aR expression on a neutrophil; and instructions for using the reagent for providing a prognosis to the subject. In some embodiments, the reagent is an anti-C5aR antibody. In some embodiments, the antibody is labeled with a fluorescent label. In some embodiments, the kit further comprises reagents for using fluorescence activated cell sorting to detect the antibody. In some embodiments, the kit further comprises a normal standard for C5aR expression. In some embodiments, the kit further comprises instructions for using the normal standard for quantitating the level of C5aR expression on neutrophils of the subject.

In still further embodiments, the present invention provides a method of treating sepsis, comprising providing a reagent capable of blocking a C5a receptor; and administering the reagent to a subject suffering from sepsis. In some preferred embodiments, the administering results in a decrease in symptoms of sepsis in the subject. In some embodiments, the reagent is a small molecule antagonist of the C5a receptor (e.g., including, but not limited to, F[OPdChaWR] and MeFKPdChaFR). In other embodiments, the reagent is an antibody specific for the C5a receptor (e.g., a monoclonal antibody).

DESCRIPTION OF THE FIGURES

FIGS. 2A-2C show the ability of neutrophils from septic animals to respond chemotactically in vitro to C5a.

FIG. 6 shows inhibition of $^{125}$I-recombinant mouse (m) C5a binding to mouse neutrophils in the presence of increasing concentrations of unlabeled mC5a or C5aRa. Data are expressed as a percent of binding values using 100 pM $^{125}$I-mC5a.

FIG. 7 shows inhibitory effects of C5aRa on chemotactic responses of mouse neutrophils to recombinant mouse C5a. FIG. 7A shows chemotactic responses of mouse neutrophils to a range of concentrations of recombinant mouse C5a in the absence (filled circles) or presence of 1.0 µM C5aRa (open circles). FIG. 7B shows blockade of chemotactic activity (using 10 nM mC5a) of mouse neutrophils in the presence of a range of concentrations of C5aRa.

DEFINITIONS

Figure 1:
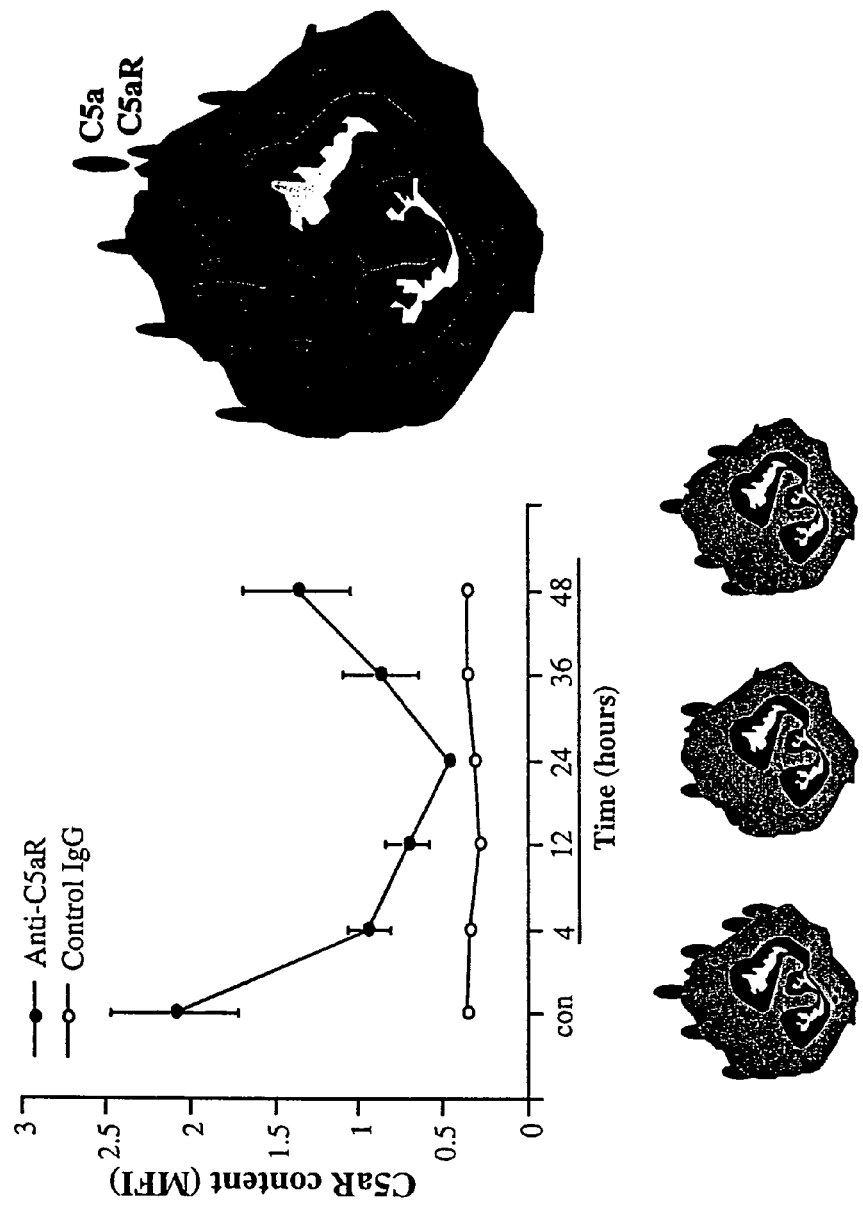
FIG. 1 shows a time course of C5aR expression on neutrophils.

The phrase "symptoms of sepsis" refers to any symptoms characteristic of a subject with sepsis including but not limited to, arterial hypotension, metabolic acidosis, fever, decreased systemic vascular resistance, tachypnea and organ dysfunction. Sepsis can result from septicemia (i.e., organisms, their metabolic end-products or toxins in the blood stream), including bacteremia (i.e., bacteria in the blood), as well as toxemia (i.e., toxins in the blood), including endotoxemia (i.e., endotoxin in the blood). The term "sepsis" also encompasses fungemia (i.e., fungi in the blood), viremia (i.e., viruses or virus particles in the blood), and parasitemia (i.e., helminthic or protozoan parasites in the blood). Thus, phenotypes associated with septicemia and septic shock (acute circulatory failure resulting from septicemia often associated with multiple organ failure and a high mortality rate) are symptoms of sepsis.

The phrase "reduces the symptoms of sepsis" refers to a qualitative or quantitative reduction in detectable symptoms, including but not limited to a detectable impact on the rate of recovery from disease or the rate of disease progression or severity.

The phrase "at risk for sepsis" in reference to a subject is herein defined as a subject predisposed to the development of sepsis by virtue of the subject's medical status, including but not limited to such factors as infection, trauma (e.g., abdominal perforation, such as by a gun shot wound), surgery (e.g., intestinal surgery), and invasive procedures (e.g., placement of a catheter, etc.) and the like.

As used herein, the term "subject diagnosed with sepsis" refers to subject that has been diagnosed with sepsis (e.g., by the presence of one or more symptoms of sepsis).

As used herein, the term "antigen" refers to any agent (e.g., any substance, compound, molecule [including macromolecules], or other moiety), that is recognized by an antibody, while the term "immunogen" refers to any agent (e.g., any substance, compound, molecule [including macromolecules], or other moiety) that can elicit an immunological response in an individual. These terms may be used to refer to an individual macromolecule or to a homogeneous or heterogeneous population of antigenic macromolecules. It is intended that the term encompasses protein and peptide molecules or at least one portion of a protein or peptide molecule, which contains one or more epitopes. In many cases, antigens are also immunogens, thus the term "antigen" is often used interchangeably with the term "immunogen." The substance may then be used as an antigen in an assay to detect the presence of appropriate antibodies in the serum of the immunized animal.

The term "specific for" when used in reference to the interaction of an antibody and a protein or peptide means that the interaction is dependent upon the presence of a particular structure (i.e., the antigenic determinant or epitope) on the protein; in other words the antibody is recognizing and binding to a specific protein structure rather than to proteins in general (i.e. non-specific or background binding).

The term "not reactive with" when used in reference to the potential interaction of an antibody and a protein or peptide means that the antibody does not recognize or bind specifically to that particular protein (i.e. binding is at background levels).

The term "operably linked" refers to an arrangement of elements wherein the components so described are configured so as to perform their usual function. Thus, control sequences operably linked to a coding sequence are capable of effecting the expression of the coding sequence. The control sequences need not be contiguous with the coding sequence, so long as they function to direct the expression.

As used herein, the terms "C5a peptide", "C5a protein", and "complement component C5a peptide" all refer to the complement component peptide in animals which is cleaved from the amino terminus of complement component C5 when the complement system is activated. Examples of animals with this protein include, but are not limited to, mice, rats, cows, pigs, and humans. This definition also includes peptides with synthetic sequences which share substantial homology to naturally occurring C5a peptides. An example of this type of sequence, includes, but is not limited to, the sequence disclosed in Mandecki et al., Proc Natl Acad Sci USA. Jun;82(11):3543-7(1985).

As used herein, the terms "C5aR" or C5a receptor" refer to the receptor for the complement component peptide in animals which is cleaved from the amino terminus of complement component C5 when the complement system is activated.

As used herein, the phrase "anti-C5a antibody" refers to antibodies which are specific for complement component C5a peptide, or portions thereof.

As used herein, the term "anti-C5aR" refers to antibodies that specifically bind to the C5aR.

As used herein, the term "adjuvant" is defined as a substance known to increase the immune response to other antigens when administered with other antigens. If adjuvant is used, it is not intended that the present invention be limited to any particular type of adjuvant—or that the same adjuvant, once used, be used all the time. It is contemplated that adjuvants may be used either separately or in combination. The present invention contemplates all types of adjuvant, including but not limited to agar beads, aluminum hydroxide or phosphate (alum), Incomplete Freund's Adjuvant, as well as Quil A adjuvant commercially available from Accurate Chemical and Scientific Corporation, Gerbu adjuvant also commercially available (GmDP; C.C. Biotech Corp.), and bacterin (i.e., killed preparations of bacterial cells).

DESCRIPTION OF THE INVENTION

The present invention relates to methods and compositions for the diagnosis and treatment of sepsis. In particular, the present invention relates to compositions and methods for the detection of C5aR expression. The diagnostic methods of the present invention find use in the diagnosis of individuals at increased risk of developing sepsis, as well as methods of monitoring sepsis treatments. In other embodiments, the present invention provides methods of treating sepsis by blocking the C5aR.

I. C5a and C5aR in Sepsis

The complement system is a complex group of proteins present in body fluids that, working together with antibodies or other factors, plays an important role as mediators of immune, allergic, immunochemical and immunopathological reactions. Activation of the complement system can result in a wide range of reactions such as lysis of various kinds of cells, bacteria and protozoa, inactivation of viruses, and the direct mediation of inflammatory processes. Through the hormone-like activity of several of its components, the complement system can recruit and enlist the participation of other humoral and cellular effector systems. These in turn can induce directed migration of leukocytes, trigger histamine release from mast cells, and stimulate the release of lysosomal constituents from phagocytes.

The complement system consists of at least twenty distinct plasma proteins capable of interacting with each other, with antibodies, and with cell membranes. Many of these proteins, when activated, combine with still others to form enzymes that cleave and activate still other proteins in the system. The sequential activation of these proteins follows two main pathways, the classical pathway and the alternative pathway. Both pathways use a common terminal trunk that leads to cell lysis or virus inactivation.

The classical pathway can be activated by antigen-antibody complexes, aggregated immunoglobulins and non-immunological substances such as DNA and trypsin-like enzymes. The classical pathway includes activation of C1, C4, C2 and C3. These components can be grouped into two functional units: C1 or recognition unit; and C4, C2 and C3 or activation unit. Five additional components denominated C5, C6, C7, C8, and C9 define the membrane attack unit forming the terminal trunk common to both pathways.

C5a peptide, also called anaphylatoxin, is a complement component peptide which is cleaved from the amino terminus of component C5 when the complement system is activated. C5a peptide has been shown to stimulate contraction of smooth muscle, enhance vascular permeability, promote the synthesis and release of other mediators including leukotrienes, prostaglandins, platelet-activating factor, and histamine. In vivo, C5a peptide results in the accumulation of polymorphonuclear leukocytes (PMN) (i.e. neutrophils) and macrophages at the site of inflammation, one of the hallmark events of an acute inflammatory response. In vitro, C5a peptide is a potent chemotaxin for leukocytes, most notably PMN and macrophages, and it activates PMN causing them to release a variety of hydrolytic enzymes and to generate oxygen radicals. These latter phenomena are thought to be responsible not only for the killing of microorganisms but for much of the tissue destruction that takes place in inflammatory situations.

There is abundant evidence that in sepsis, complement activation, production of cytokines, and unregulated inflammatory responses occurs. It is well established in humans with sepsis that complement activation and complement consumption have occurred, as defined by loss of whole hemolytic activity of serum complement (CH50) and the presence of C5a peptide in serum (Koehl, J., Bitter-Suermann, D., Anaphylatoxins. Complement in health and disease., Edited by Whaley, K., Loos, M., Weiler, J. M., Kluwer Academic publishers, pp 299-324, (1993), and Solomkin et al., Surgery 90:319-327, (1981)).

Interaction of C5a peptide with C5a receptor (C5aR) leads to phosphorylation, of serine residues of the receptor, followed by rapid internalization of the receptor-ligand complex, dephosphorylation of the receptor and its recycling back to the surface of the cell. All of this occurs fairly rapidly. Furthermore, the maximal C5a-induced $H_2O_2$ response of the neutrophil requires that only a fraction of C5aR be occupied with ligand (Van Epps, et al., J. Immunol. 150:246-252 (1993)). Neutrophils stimulated with C5a peptide become refractory ("deactivated") to further stimulation with this peptide; following exposure to high doses of C5a peptide, global deactivation to chemotactic peptides occurs (Ward and Becker, *J. Exp. Med.* 127:693-709 (1968)). There is clinical evidence that blood neutrophils from humans with early sepsis lose functional responsiveness to C5a peptide and in the latter phases of sepsis lose responsiveness to structurally different chemotaxins such as the bacterial chemotactic factor (Solomkin et al., *Surgery* 90:319-327 (1981)). It has also been reported that C5 deficient mice demonstrate somewhat prolonged survival times when sepsis is induced, but ultimately all animals succumbed to the sepsis syndrome (Olson et al., *Ann. Surg.* 202:771-776 (1985)).

C5aR content in various tissues (lung, liver, kidney and heart) is increased during the onset of sepsis, defined by up-regulation of C5aR (protein and mRNA) (J. Clin. Invest. 110:101-8, 2002). After binding of C5a to C5aR on neutrophils, the ligand/receptor complex is rapidly internalized and C5aR is ultimately recycled to the cell surface. This has been repeatedly demonstrated using in vitro experiments with human neutrophils.

II. Diagnostic Applications

Figure 2:
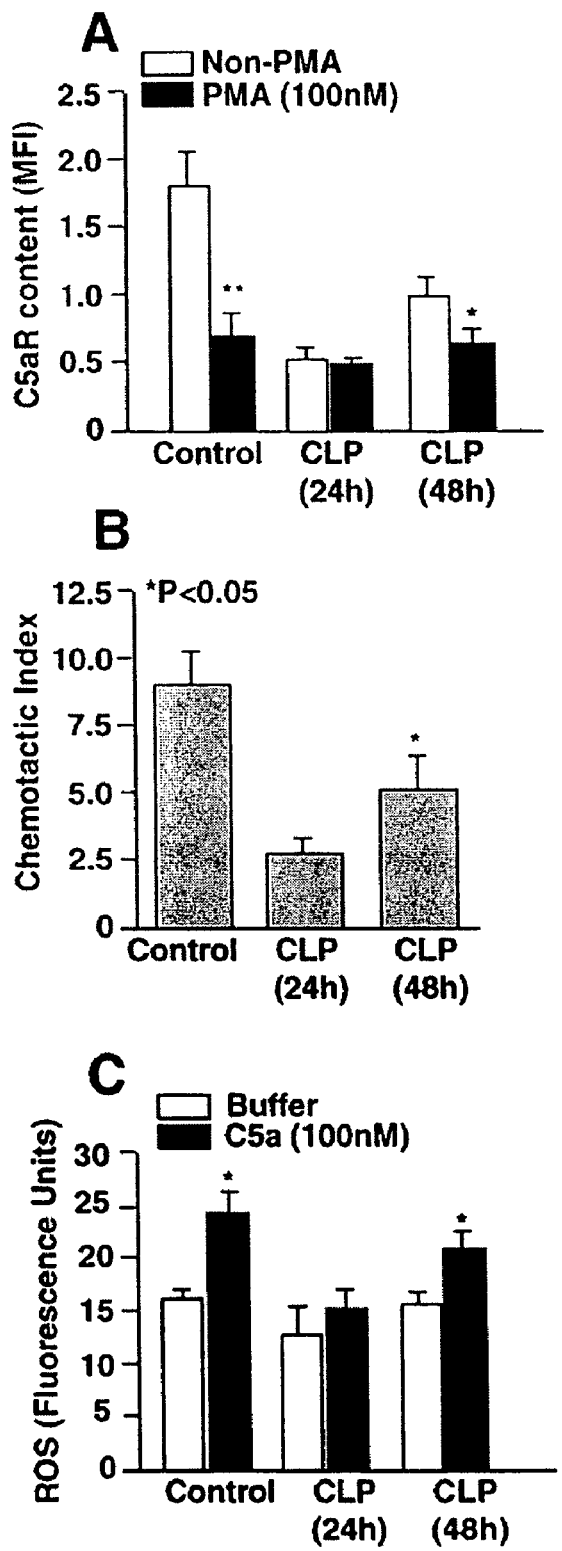

C5aR content in various tissues (lung, liver, kidney and heart) is increased during the onset of sepsis, defined by up-regulation of C5aR (protein and mRNA) (J. Clin. Invest. 110:101-8, 2002). Experiments conducted during the course of development of the present invention (See example 1) utilizing rat neutrophils from septic animals after cecal ligation/puncture (CLP) showed that blood neutrophils demonstrate a different pattern. The total amount of C5aR protein in and on blood neutrophils did not change during sepsis, nor did messenger RNA for C5aR. Experiments conducted during the course of development of the present invention demonstrated, however, that surface expression of C5aR on blood neutrophils significantly fell, starting as early as 4 hours after the onset of CLP-induced sepsis, reached a nadir at 24 hours, and slowly increased thereafter (FIG. 1). The loss of C5aR on the neutrophil surface was due to internalization of C5aR triggered by contact with C5a in the blood. The ability of neutrophils from septic animals to respond chemotactically in vitro to C5a was depressed, inversely correlated with the number of C5aR on the surfaces of neutrophils (FIG. 2A). The data show that neutrophils with higher numbers of C5aR during sepsis are associated with enhanced survival of the animals, while the opposite is true with neutrophils that have low numbers of C5aR. Another functional parameter is the ability of neutrophils to generate reactive oxygen species (ROS), which are required for bacterial killing by neutrophils. Experiments conducted during the course of development of the present invention demonstrated a positive correlation between the ability of neutrophils to produce ROS and higher C5aR levels on neutrophils (FIG. 2B).

Figure 12:
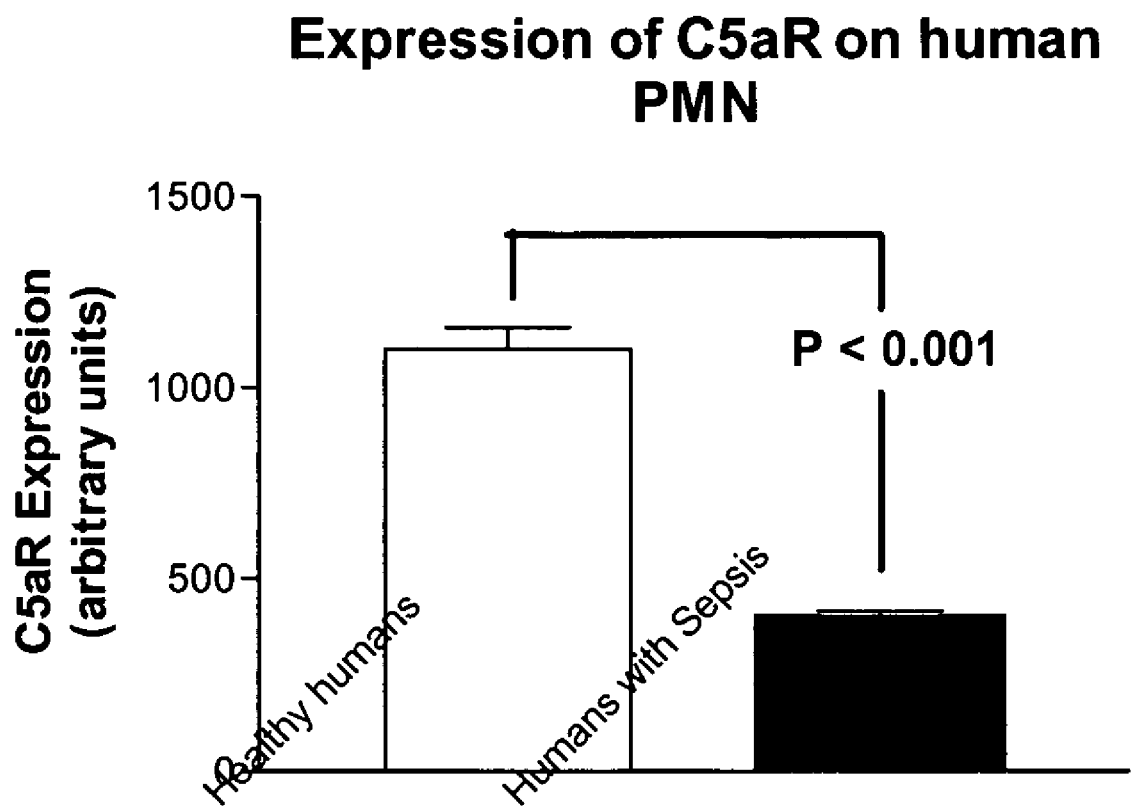
FIG. 12 shows the expression of C5aR on human PMN.

Further experiments conducted during the course of the present invention (See FIG. 12) demonstrated a correlation between expression of C5aR on human neutrophils (PMNs) with sepsis. Flow cytometry was used to determine the level of expression of C5aR on human PMNs in healthy humans and humans with sepsis. The expression levels were increased in healthy humans.

Currently, there are no highly reliable single prognostic indicators for septic patients. The known laboratory methods to detect C5aR on blood neutrophils utilize '251-C5a binding, requiring the isolation of neutrophils, the processing of which can alter C5aR content. These procedures are very time consuming and also require larger volumes (40 ml or more) of blood samples.

Accordingly, in some embodiments, the present invention provides methods of characterizing (e.g., providing a prognosis) sepsis based on the level of C5aR expression on neutrophils. In other embodiments, the methods of the present invention are used in the diagnosis of sepsis (e.g., based on expression levels of C5aR on neutrophils). In some embodiments, the methods of the present invention are used in combination with other diagnostic methods useful in diagnosing sepsis. In still further embodiments, the methods of the present invention are used in monitoring the recovery of an individual diagnosed with sepsis.

The methods of the present invention involve common laboratory technologies (Flow Cytometry), and, in some embodiments, utilize antibody-based detection of C5aR on blood neutrophils (See Example 1 for a description of one embodiment of the assay). In some embodiments, a reference standard for C5aR content on blood neutrophils from normal humans is used for comparison. The diagnostic method of the present invention allows for the detection of C5aR on whole blood cells, eliminating the time consuming step of isolating neutrophils. This provides the advantages of requiring only a minimal amount of blood (as little as 100 µl). In addition, the diagnostic method of the present invention is much more rapid than methods requiring the isolation of neutrophils, and, in some preferred embodiments, requires only one hour to perform.

In some embodiments, the level of C5aR expression is used to provide a prognosis to a patient suspected of having, or diagnosed with, sepsis. As described above, experiments conducted during the course of development of the present invention demonstrated that the level of C5aR expression on neutrophils correlated with an improved prognosis in sepsis. The appropriate course of treatment can then be chosen. For example, if a patient is found to have lower levels of C5aR expression, more aggressive treatment may be started earlier. Alternatively, in some embodiments, gene therapy or other pharmaceuticals may be used to increase the levels of C5aR expression.

III. Generating Antibodies to C5aR Peptides

The present invention contemplates monoclonal, polyclonal, and humanized antibodies to C5aR peptides and fragments thereof. Monoclonal antibodies useful in this invention are obtained, for example, by well known hybridoma methods. In one embodiment, an animal is immunized with a preparation containing C5aR peptides. A fused cell hybrid is then formed between antibody-producing cells from the immunized animal and an immortalizing cell such as a myeloma. In one embodiment, antibodies of the present invention are produced by murine hybridomas formed by fusion of mouse myeloma or hybridoma which does not secrete antibody with murine spleen cells which secrete antibodies obtained from mice immunized against C5aR or peptide fragments thereof.

In some embodiments, mice are immunized with a primary injection of C5aR peptides, followed by a number of boosting injections. During or after the immunization procedure, sera of the mice may be screened to identify mice in which a substantial immune response to the C5aR peptides has been evoked. From the selected mice, spleen cells are obtained and fusions are performed. Suitable fusion techniques include, but are not limited to, the Sendai virus technique (Kohler, G. and Milstein, C., *Nature* 256:495 (1975)) or the polyethylene glycol method (Kennet, R. H., "*Monoclonal Antibodies, Hybridoma—A New Dimension in Biological Analysis*," Plenum Press, NY (1980)).

The hybridomas are then screened for production of anti-C5aR antibodies. Suitable screening techniques include, but are not limited to, solid phase radioimmunoassay. A solid phase immunoadsorbent is prepared by coupling C5aR peptides to an insoluble matrix. The immunoadsorbent is brought into contact with culture supernatants of hybridomas. After a period of incubation, the solid phase is separated from the supernatants, then contacted with a labeled antibody against murine immunoglobulin. Label associated with the immunoadsorbent indicates the presence of hybridoma products reactive with C5aR peptides.

In preferred embodiments the monoclonal anti-C5aR antibodies are produced in large quantities by injecting anti-C5aR antibody producing hybridoma cells into the peritoneal cavity of mice and, after an appropriate time, harvesting acites fluid from the mice which yield a high titer of homogenous antibody. The monoclonal antibodies are isolated there from. Alternatively, the antibodies are produced by culturing anti-C5aR antibody producing cells in vitro and isolating secreted monoclonal anti-C5aR antibodies from the cell culture medium directly.

Another method of forming antibody-producing cells is by viral or oncogenic transformation. For example, a B-lymphocyte which produces anti-C5aR specific antibody is infected and transformed with a virus, such as the Epstein-Barr virus, to give an immortal antibody-producing cell (Kozbon and Roder, *Immunol. Today* 4:72-79 (1983)).

The present invention also contemplates anti-C5aR polyclonal antibodies. Polyclonal antibodies can be prepared by immunizing an animal with a crude preparation of C5aR peptides, or purified C5aR peptides. The animal is maintained under conditions whereby antibodies reactive with the components of the peptides are produced. (See e.g. Elzaim et al., *Infect. Immun.* 66:2170-9 (1998)). Typically the animal is "boosted" by additional immunizations to increase the antibody titer. In one method, blood is collected from the animal upon reaching a desired titer of antibodies. The serum containing the polyclonal antibodies (antisera) is separated from the other blood components. The polyclonal antibody-containing serum may be further separated into fractions of particular types of antibodies (e.g. IgG or IgM) or monospecific antibodies can be affinity purified from polyclonal antibody containing serum. In another method, the immunized animal is a bird. In this' method antibodies (IgY) are collected from egg yolks. The egg yolk is separated from the yolk lipid and non-antibody proteinaceous matter, recovering the IgY anti-C5a antibodies in purified form (See e.g. U.S. Pat. No. 4,357,272 to Polson and U.S. Pat. No. 5,904,922 to Carroll; each of which is herein incorporated by reference).

The present invention also contemplates humanized antibodies (e.g., substantially non-immunogenic antibodies). Such antibodies are particularly useful in treating human subjects. Chimeric and 'reshaped' humanized anti-C5aR antibodies may be produced according to techniques known in the art (see e,g. U.S. Pat. No. 5,585,089 to Queen et al., and Kettleborough, et al., *Protein Engineering*, vol. 4, no.7, pp 773-783, 1991; each of which is herein incorporated by reference). In one embodiment, humanized anti-C5aR chimeric antibodies are produced using a combinatorial approach (see e.g. U.S. Pat. No. 5,565,332 to Hoogenboom et al. and U.S. Pat. No. 5,658,727 to Barbas et al.; each of which is herein incorporated by reference). The present invention also contemplates single polypeptide chain binding molecules which have binding specificity and affinity substantially similar to the binding specificity and affinity of the light and heavy chain aggregate variable region of an anti-C5aR antibody (see e.g. U.S. Pat. No. 5,260,203 to Ladner et al.; herein incorporated by reference).

IV. Drug Screening

In some embodiments, the detection methods of the present invention may be used to screen new therapeutics (e.g., treatments for sepsis). For example, in some embodiments, candidate compounds are contacted with neutrophils expressing low or high amounts of C5aR and the ability of the candidate compounds to increase the level of C5aR expression is evaluated (e.g., using the methods of the present invention). In some embodiments, candidate compounds are screened for their ability to improve the prognosis of patients with sepsis. In some embodiments, candidate compounds are small molecules. In other embodiments, candidate compounds are C5aR blocking agents (See below) such as C5aR antibodies or antagonists.

The test compounds of the present invention can be obtained using any of the numerous approaches in combinatorial library methods known in the art, including biological libraries; peptoid libraries (libraries of molecules having the functionalities of peptides, but with a novel, non-peptide backbone, which are resistant to enzymatic degradation but which nevertheless remain bioactive; see, e.g., Zuckennann et al., J. Med. Chem. 37: 2678-85 [1994]); spatially addressable parallel solid phase or solution phase libraries; synthetic library methods requiring deconvolution; the 'one-bead one-compound' library method; and synthetic library methods using affinity chromatography selection. The biological library and peptoid library approaches are preferred for use with peptide libraries, while the other four approaches are applicable to peptide, non-peptide oligomer or small molecule libraries of compounds (Lam (1997) Anticancer Drug Des. 12:145).

Examples of methods for the synthesis of molecular libraries can be found in the art, for example in: DeWitt et al., Proc. Natl. Acad. Sci. U.S.A. 90:6909 [1993]; Erb et al., Proc. Nad. Acad. Sci. USA 91:11422 [1994]; Zuckermann et al., J. Med. Chem. 37:2678 [1994]; Cho et al., Science 261:1303 [1993]; Carrell et al., Angew. Chem. Int. Ed. Engl. 33.2059 [1994]; Carell et al., Angew. Chem. Int. Ed. Engl. 33:2061 [1994]; and Gallop et al., J. Med. Chem. 37:1233 [1994].

Libraries of compounds may be presented in solution (e.g., Houghten, Biotechniques 13:412-421 [1992]), or on beads (Lam, Nature 354:82-84 [1991]), chips (Fodor, Nature 364: 555-556 [1993]), bacteria or spores (U.S. Pat. No. 5,223,409; herein incorporated by reference), plasmids (Cull et al., Proc. Nad. Acad. Sci. USA 89:18651869 [1992]) or on phage (Scott and Smith, Science 249:386-390 [1990]; Devlin Science 249: 404-406 [1990]; Cwirla et al., Proc. Natl. Acad. Sci. 87:6378-6382 [1990]; Felici, J. Mol. Biol. 222:301 [1991]).

In other embodiments, candidate compounds are screened in animal models of sepsis (e.g., the CLP model disclosed herein). In some embodiments, candidate compounds identified as having activity in the in vitro drug screening methods described above are testing in animal models. Candidate compounds are analyzed in the animal model for their ability to increase survival in animals given experimental sepsis.

In other embodiments, the detection methods of the present invention are used to monitor the effectiveness of new or existing treatments for sepsis. Patients receiving treatment for sepsis are monitored on a regular basis for their levels of C5aR expression. Preferred treatments are those that increase the level of expression of C5aR.

V. Gene Therapy

The present invention also provides methods and compositions suitable for gene therapy to alter C5aR expression, production, or function. In some embodiments, it is contemplated that the gene therapy is performed by providing a subject with additional C5aR receptors on neutrophils to aid the prevention and/or treatment of sepsis. Subjects in need of such therapy may be identified by the methods described above (e.g., the diagnostic methods described above).

Viral vectors commonly used for in vivo or ex vivo targeting and therapy procedures are DNA-based vectors and retroviral vectors. Methods for constructing and using viral vectors are known in the art (See e.g., Miller and Rosman, BioTech., 7:980-990 [1992]). Preferably, the viral vectors are replication defective, that is, they are unable to replicate autonomously in the target cell. In general, the genome of the replication defective viral vectors that are used within the scope of the present invention lack at least one region that is necessary for the replication of the virus in the infected cell. These regions can either be eliminated (in whole or in part), or be rendered non-functional by any technique known to a person skilled in the art. These techniques include the total removal, substitution (by other sequences, in particular by the inserted nucleic acid), partial deletion or addition of one or more bases to an essential (for replication) region. Such techniques may be performed in vitro (i.e., on the isolated DNA) or in situ, using the techniques of genetic manipulation or by treatment with mutagenic agents.

Preferably, the replication defective virus retains the sequences of its genome that are necessary for encapsidating the viral particles. DNA viral vectors include an attenuated or defective DNA viruses, including, but not limited to, herpes simplex virus (HSV), papillomavirus, Epstein Barr virus (EBV), adenovirus, adeno-associated virus (AAV), and the like. Defective viruses, that entirely or almost entirely lack viral genes, are preferred, as defective virus is not infective after introduction into a cell. Use of defective viral vectors allows for administration to cells in a specific, localized area, without concern that the vector can infect other cells. Thus, a specific tissue can be specifically targeted. Examples of particular vectors include, but are not limited to, a defective herpes virus 1 (HSV1) vector (Kaplitt et al., Mol. Cell. Neurosci., 2:320-330 [1991]), defective herpes virus vector lacking a glycoprotein L gene (See e.g., Patent Publication RD 371005 A), or other defective herpes virus vectors (See e.g., WO 94/21807; and WO 92/05263); an attenuated adenovirus vector, such as the vector described by Stratford-Perricaudet et al. (J. Clin. Invest., 90:626-630 [1992]; See also, La Salle et al., Science 259:988-990 [1993]); and a defective adeno-associated virus vector (Samulski et al., J. Virol., 61:3096-3101 [1987]; Samulski et al., J. Virol., 63:3822-3828 [1989]; and Lebkowski et al., Mol. Cell. Biol., 8:3988-3996 [1988]).

Preferably, for in vivo administration, an appropriate immunosuppressive treatment is employed in conjunction with the viral vector (e.g., adenovirus vector), to avoid immuno-deactivation of the viral vector and transfected cells. For example, immunosuppressive cytokines, such as interleukin-12 (IL-12), interferon-gamma (IFN-γ), or anti-CD4 antibody, can be administered to block humoral or cellular immune responses to the viral vectors. In addition, it is advantageous to employ a viral vector that is engineered to express a minimal number of antigens.

In a preferred embodiment, the vector is an adenovirus vector. Adenoviruses are eukaryotic DNA viruses that can be modified to efficiently deliver a nucleic acid of the invention to a variety of cell types. Various serotypes of adenovirus exist. Of these serotypes, preference is given, within the scope of the present invention, to type 2 or type 5 human adenoviruses (Ad 2 or Ad 5), or adenoviruses of animal origin (See e.g., WO94/26914). Those adenoviruses of animal origin that can be used within the scope of the present invention include, for example, adenoviruses of canine, bovine, murine (e.g., Mav1, Beard et al., Virol., 75-81 [1990]), ovine, porcine, avian, and simian (e.g., SAV) origin. Preferably, the adenovirus of animal origin is a canine adenovirus, more preferably a CAV2 adenovirus (e.g. Manhattan or A26/61 strain (ATCC VR-800)).

Preferably, the replication defective adenoviral vectors of the invention comprise the ITRs, an encapsidation sequence and the nucleic acid of interest. Still more preferably, at least the E1 region of the adenoviral vector is non-functional. The deletion in the E1 region preferably extends from nucleotides 455 to 3329 in the sequence of the Ad5 adenovirus (PvuII-BglII fragment) or 382 to 3446 (HinfII-Sau3A fragment). Other regions may also be modified, in particular the E3 region (e.g., WO95/02697), the E2 region (e.g., WO94/28938), the E4 region (e.g., WO94/28152, WO94/12649 and WO95/02697), or in any of the late genes L1-L5.

In a preferred embodiment, the adenoviral vector has a deletion in the E1 region (Ad 1.0). Examples of E1-deleted adenoviruses are disclosed in EP 185,573, the contents of which are incorporated herein by reference. In another preferred embodiment, the adenoviral vector has a deletion in the E1 and E4 regions (Ad 3.0). Examples of E1/E4-deleted adenoviruses are disclosed in WO95/02697 and WO96/22378. In still another preferred embodiment, the adenoviral vector has a deletion in the E1 region into which the E4 region and the nucleic acid sequence are inserted.

The replication defective recombinant adenoviruses according to the invention can be prepared by any technique known to the person skilled in the art (See e.g., Levrero et al., Gene 101:195 [1991]; EP 185 573; and Graham, EMBO J., 3:2917 [1984]). In particular, they can be prepared by homologous recombination between an adenovirus and a plasmid which carries, inter alia, the DNA sequence of interest. The homologous recombination is accomplished following co-transfection of the adenovirus and plasmid into an appropriate cell line. The cell line that is employed should preferably (i) be transformable by the elements to be used, and (ii) contain the sequences that are able to complement the part of the genome of the replication defective adenovirus, preferably in integrated form in order to avoid the risks of recombination. Examples of cell lines that may be used are the human embryonic kidney cell line 293 (Graham et al., J. Gen. Virol., 36:59 [1977]), which contains the left-hand portion of the genome of an Ad5 adenovirus (12%) integrated into its genome, and cell lines that are able to complement the E1 and E4 functions, as described in applications WO94/26914 and WO95/02697. Recombinant adenoviruses are recovered and purified using standard molecular biological techniques, that are well known to one of ordinary skill in the art.

The adeno-associated viruses (AAV) are DNA viruses of relatively small size that can integrate, in a stable and site-specific manner, into the genome of the cells that they infect. They are able to infect a wide spectrum of cells without inducing any effects on cellular growth, morphology or differentiation, and they do not appear to be involved in human pathologies. The AAV genome has been cloned, sequenced and characterized. It encompasses approximately 4700 bases and contains an inverted terminal repeat (ITR) region of approximately 145 bases at each end, which serves as an origin of replication for the virus. The remainder of the genome is divided into two essential regions that carry the encapsidation functions: the left-hand part of the genome, that contains the rep gene involved in viral replication and expression of the viral genes; and the right-hand part of the genome, that contains the cap gene encoding the capsid proteins of the virus.

The use of vectors derived from the AAVs for transferring genes in vitro and in vivo has been described (See e.g., WO 91/18088; WO 93/09239; U.S. Pat. No. 4,797,368; U.S. Pat. No. 5,139,941; and EP 488 528, all of which are herein incorporated by reference). These publications describe various AAV-derived constructs in which the rep and/or cap genes are deleted and replaced by a gene of interest, and the use of these constructs for transferring the gene of interest in vitro (into cultured cells) or in vivo (directly into an organism). The replication defective recombinant AAVs according to the invention can be prepared by co-transfecting a plasmid containing the nucleic acid sequence of interest flanked by two AAV inverted terminal repeat (ITR) regions, and a plasmid carrying the AAV encapsidation genes (rep and cap genes), into a cell line that is infected with a human helper virus (for example an adenovirus). The AAV recombinants that are produced are then purified by standard techniques.

In another embodiment, the gene can be introduced in a retroviral vector (e.g., as described in U.S. Pat. Nos. 5,399, 346, 4,650,764, 4,980,289 and 5,124,263; Mann et al., Cell 33:153 [1983]; Markowitz et al., J. Virol., 62:1120 [1988]; PCT/US95/14575; EP 453242; EP178220; Bernstein et al. Genet. Eng., 7:235 [1985]; McCormick, BioTechnol., 3:689 [1985]; WO 95/07358; and Kuo et al., Blood 82:845 [1993]; each of which is herein incorporated by reference). The retroviruses are integrating viruses that infect dividing cells. The retrovirus genome includes two LTRs, an encapsidation sequence and three coding regions (gag, pol and env). In recombinant retroviral vectors, the gag, pol and env genes are generally deleted, in whole or in part, and replaced with a heterologous nucleic acid sequence of interest. These vectors can be constructed from different types of retrovirus, such as, HIV, MoMuLV ("murine Moloney leukemia virus" MSV ("murine Moloney sarcoma virus"), HaSV ("Harvey sarcoma virus"); SNV ("spleen necrosis virus"); RSV ("Rous sarcoma virus") and Friend virus. Defective retroviral vectors are also disclosed in WO 95/02697; herein incorporated by reference).

In general, in order to construct recombinant retroviruses containing a nucleic acid sequence, a plasmid is constructed that contains the LTRs, the encapsidation sequence and the coding sequence. This construct is used to transfect a packaging cell line, which cell line is able to supply in trans the retroviral functions that are deficient in the plasmid. In general, the packaging cell lines are thus able to express the gag, pol and env genes. Such packaging cell lines have been described in the prior art, in particular the cell line PA317 (U.S. Pat. No. 4,861,719, herein incorporated by reference), the PsiCRIP cell line (See, WO 90/02806; herein incorporated by reference), and the GP+envAm-12 cell line (See, WO 89/07150; herein incorporated by reference). In addition, the recombinant retroviral vectors can contain modifications within the LTRs for suppressing transcriptional activity as well as extensive encapsidation sequences that may include a part of the gag gene (Bender et al., J. Virol., 61:1639 [1987]). Recombinant retroviral vectors are purified by standard techniques known to those having ordinary skill in the art.

Alternatively, the vector can be introduced in vivo by lipofection. For the past decade, there has been increasing use of liposomes for encapsulation and transfection of nucleic acids in vitro. Synthetic cationic lipids designed to limit the difficulties and dangers encountered with liposome mediated transfection can be used to prepare liposomes for in vivo transfection of a gene encoding a marker (Felgner et. al., Proc. Natl. Acad. Sci. USA 84:7413-7417 [1987]; See also, Mackey, et al., Proc. Natl. Acad. Sci. USA 85:8027-8031 [1988]; Ulmer et al., Science 259:1745-1748 [1993]). The use of cationic lipids may promote encapsulation of negatively charged nucleic acids, and also promote fusion with negatively charged cell membranes (Felgner and Ringold, Science 337:387-388 [1989]). Particularly useful lipid compounds and compositions for transfer of nucleic acids are described in WO 95/18863 and WO 96/17823, and in U.S. Pat. No. 5,459, 127, each of which is herein incorporated by reference.

Other molecules are also useful for facilitating transfection of a nucleic acid in vivo, such as a cationic oligopeptide (e.g., WO95/21931; herein incorporated by reference), peptides derived from DNA binding proteins (e.g., WO96/25508; herein incorporated by reference), or a cationic polymer (e.g., WO95/21931; herein incorporated by reference).

It is also possible to introduce the vector in vivo as a naked DNA plasmid. Methods for formulating and administering naked DNA to mammalian muscle tissue are disclosed in U.S. Pat. Nos. 5,580,859 and 5,589,466, both of which are herein incorporated by reference.

DNA vectors for gene therapy can be introduced into the desired host cells by methods known in the art, including but not limited to transfection, electroporation, microinjection, transduction, cell fusion, DEAE dextran, calcium phosphate precipitation, use of a gene gun, or use of a DNA vector transporter (See e.g., Wu et al., J. Biol. Chem., 267:963-967 [1992]; Wu and Wu, J. Biol. Chem., 263:14621-14624 [1988]; and Williams et al., Proc. Natl. Acad. Sci. USA 88:2726-2730 [1991]). Receptor-mediated DNA delivery approaches can also be used (Curiel et al., Hum. Gene Ther., 3:147-154 [1992]; and Wu and Wu, J. Biol. Chem., 262:4429-4432 [1987]).

VI. Treatment of Sepsis

The present invention is not limited to a particular mechanism. Indeed, an understanding of the mechanism is not necessary to practice the present invention. Nonetheless, it is contemplated, based on the experiments disclosed herein (See e.g., Examples 2 and 3), that blockade of the C5a receptor (C5aR) results in a beneficial effect in the outcome of sepsis. Accordingly, in some embodiments, the present invention provides methods of treating sepsis by blocking the C5aR receptor (e.g., with a C5aR antibody or antagonist).

The CLP mouse model was used to investigate the effect of C5aR blockage (See Examples 2 and 3). Blockade of C5aR by C5aR antagonists resulted in improved survival compared to control animals. The activity of the C5aR antagonist was also confirmed in vitro by chemotaxis experiments, showing significantly reduced chemotactic responses of mouse neutrophils to mouse C5a when the cells were pre-incubated with the C5aR antagonist. In addition, blockade of C5aR by this antagonist resulted in significantly reduced lung injury in a model of immune complex induced lung injury as measured by leakage of $^{125}$I-labeled bovine serum albumin (BSA). Administration of an antibody against C5aR resulted in increased survival compared to the group of animals injected with irrelevant IgG.

Thus, experiments conducted during the course of development of the present invention demonstrated that survival in sepsis in rodents can be significantly improved by blockade of C5aR. Accordingly, in some embodiments, the present invention provides methods of treating or preventing sepsis and associated organ damage by blocking C5aR. C5aR may be blocked using any suitable blocking agent, including, but not limited to, specific antagonists (e.g., small molecule antagonists) or specific antibodies directed against C5aR.

Accordingly, in some embodiments, C5aR blocking therapy is used to treat patients at high risk of developing sepsis (e.g., ICU patients after trauma or laparotomy). In other embodiments, patients judged to be in the early phases of a developing a septic syndrome are treated with C5aR blocking reagents to lower the harmful effects of C5a triggered by the increased amount of C5aR in organs in the early onset of sepsis. In yet other embodiments, C5aR blocking reagents are used in patients with fully developed septic syndrome to prevent further harmful organ effects induced by C5a. The present invention is not limited to a particular mechanism. Indeed, an understanding of the mechanism is not necessary to practice the present invention. Nonetheless, it is contemplated that C5aR blockade prevents patients from multi-organ damage caused by harmful effects of C5a linked to increased C5aR expression in lung, liver, kidney and heart.

The present invention is not limited to a particular C5aR blockage agent. Any suitable agent may be utilized. For example, in some embodiments, an antibody against C5aR is utilized. Is some embodiments, the antibody is humanized or fully human (See e.g., above section describing antibodies).

In other embodiments, the blocking agent is a C5aR antagonist (e.g., a small molecule antagonist). In some embodiments, the antagonist is F[OPdChaWR] (Wong et al., (1998) *J. Med. Chem.* 41,3417-3425; herein incorporated by reference). In other embodiments, the hexapeptide MeFKP-dChaFR (Mollison et al., (1992) *FASEB J* 6,A2058; Drapeau et al., (11993) *Biochem. Pharmacol.* 45,1289-1299; each of which is herein incorporated by reference) or variants thereof (Konteatis et al., (1994) *J. Immunol.* 153,4200-4205; herein incorporated by reference) are utilized as antagonists. Additional antagonists may be identified using the drug screening methods disclosed herein, or other suitable methods.

The present invention is not limited to the treatment of sepsis with C5aR blockage. Any disease states associated with increased C5aR are contemplated for treatment with C5aR blockage. For example, in some embodiments, blockade of C5aR is used as preventative or acute therapy for organ inflammatory diseases such as autoimmune disorders, glomerulonephritis, ischemic injury of the control nervous system or heart, and adult respiratory distress syndrome (ARDS).

VII. Pharmaceutical Compositions Containing C5aR or Effectors Thereof

The present invention further provides pharmaceutical compositions which may comprise all or portions of C5aR inhibitors or antagonists of C5aR bioactivity, including antibodies, alone or in combination with at least one other agent, such as a stabilizing compound, and may be administered, for example, in any sterile, biocompatible pharmaceutical carrier, including, but not limited to, saline, buffered saline, dextrose, and water.

Pharmaceutical compositions can be administered to the patient intravenously in a pharmaceutically acceptable carrier such as physiological saline. Standard methods for intracellular delivery of peptides can be used (e.g., delivery via liposome). Such methods are well known to those of ordinary skill in the art. The formulations of this invention are useful for parenteral administration, such as intravenous, subcutaneous, intramuscular, and intraperitoneal. Therapeutic administration of a polypeptide intracellularly can also be accomplished using gene therapy as described herein.

As is well known in the medical arts, dosages for any one patient depends upon many factors, including the patient's size, body surface area, age, the particular compound to be administered, sex, time and route of administration, general health, and interaction with other drugs being concurrently administered.

Accordingly, in some embodiments of the present invention, pharmaceutical compositions can be administered to a patient alone, or in combination with other nucleotide sequences, drugs or hormones or in pharmaceutical compositions where it is mixed with excipient(s) or other pharmaceutically acceptable carriers. In one embodiment of the present invention, the pharmaceutically acceptable carrier is pharmaceutically inert. In another embodiment of the present invention, polynucleotide sequences or amino acid sequences may be administered alone to individuals subject to or suffering from a disease (e.g., sepsis).

Depending on the condition being treated, these pharmaceutical compositions may be formulated and administered systemically or locally. Techniques for formulation and administration may be found in the latest edition of "Remington's Pharmaceutical Sciences" (Mack Publishing Co, Easton Pa.). Suitable routes may, for example, include oral or transmucosal administration; as well as parenteral delivery, including intramuscular, subcutaneous, intramedullary, intrathecal, intraventricular, intravenous, intraperitoneal, or intranasal administration.

For injection, the pharmaceutical compositions of the invention may be formulated in aqueous solutions, preferably in physiologically compatible buffers such as Hanks' solution, Ringer's solution, or physiologically buffered saline. For tissue or cellular administration, penetrants appropriate to the particular barrier to be permeated are used in the formulation. Such penetrants are generally known in the art.

In other embodiments, the pharmaceutical compositions of the present invention can be formulated using pharmaceutically acceptable carriers well known in the art in dosages suitable for oral administration. Such carriers enable the pharmaceutical compositions to be formulated as tablets, pills, capsules, liquids, gels, syrups, slurries, suspensions and the like, for oral or nasal ingestion by a patient to be treated.

Pharmaceutical compositions suitable for use in the present invention include compositions wherein the active ingredients are contained in an effective amount to achieve the intended purpose. For example, an effective amount of a pharmaceutical composition may be that amount that prevents or decreases symptoms of sepsis. Determination of effective amounts is well within the capability of those skilled in the art, especially in light of the disclosure provided herein.

In addition to the active ingredients these pharmaceutical compositions may contain suitable pharmaceutically acceptable carriers comprising excipients and auxiliaries that facilitate processing of the active compounds into preparations that can be used pharmaceutically. The preparations formulated for oral administration may be in the form of tablets, dragees, capsules, or solutions.

The pharmaceutical compositions of the present invention may be manufactured in a manner that is itself known (e.g., by means of conventional mixing, dissolving, granulating, dragee-making, levigating, emulsifying, encapsulating, entrapping or lyophilizing processes).

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are carbohydrate or protein fillers such as sugars, including lactose, sucrose, mannitol, or sorbitol; starch from corn, wheat, rice, potato, etc; cellulose such as methyl cellulose, hydroxypropylmethyl-cellulose, or sodium carboxymethyl-cellulose; and gums including arabic and tragacanth; and proteins such as gelatin and collagen. If desired, disintegrating or solubilizing agents may be added, such as the cross-linked polyvinyl pyrrolidone, agar, alginic acid or a salt thereof such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, (i.e., dosage).

Pharmaceutical preparations that can be used orally include push-fit capsules made of gelatin, as well as soft, sealed capsules made of gelatin and a coating such as glycerol or sorbitol. The push-fit capsules can contain the active ingredients mixed with a filler or binders such as lactose or starches, lubricants such as talc or magnesium stearate, and, optionally, stabilizers. In soft capsules, the active compounds may be dissolved or suspended in suitable liquids, such as fatty oils, liquid paraffin, or liquid polyethylene glycol with or without stabilizers.

Compositions comprising a compound of the invention formulated in a pharmaceutical acceptable carrier may be prepared, placed in an appropriate container, and labeled for treatment of an indicated condition. Conditions indicated on the label may include treatment of condition related to sepsis.

The pharmaceutical composition may be provided as a salt and can be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, the preferred preparation may be a lyophilized powder in 1 mM-50 mM histidine, 0.1%-2% sucrose, 2%-7% mannitol at a pH range of 4.5 to 5.5 that is combined with buffer prior to use.

For any compound used in the method of the invention, the therapeutically effective dose can be estimated initially from cell culture assays. Then, preferably, dosage can be formulated in animal models (particularly murine models) to achieve a desirable circulating concentration range that adjusts drug levels.

A therapeutically effective dose refers to that amount of drug that ameliorates symptoms of the disease state. Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index, and it can be expressed as the ratio $LD_{50}/ED_{50}$. Compounds that exhibit large therapeutic indices are preferred. The data obtained from these cell culture assays and additional animal studies can be used in formulating a range of dosage for human use. The dosage of such compounds lies preferably within a range of circulating concentrations that include the $ED_{50}$ with little or no toxicity. The dosage varies within this range depending upon the dosage form employed, sensitivity of the patient, and the route of administration.

The exact dosage is chosen by the individual physician in view of the patient to be treated. Dosage and administration are adjusted to provide sufficient levels of the active moiety or to maintain the desired effect. Additional factors which may be taken into account include the severity of the disease state; age, weight, and gender of the patient; diet, time and frequency of administration, drug combination(s), reaction sensitivities, and tolerance/response to therapy. Long acting pharmaceutical compositions might be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature (See, U.S. Pat. Nos. 4,657,760; 5,206,344; or 5,225,212, each of which are herein incorporated by reference).

Experimental

The following examples are provided in order to demonstrate and further illustrate certain preferred embodiments and aspects of the present invention and are not to be construed as limiting the scope thereof.

EXAMPLE 1

Detection of C5aR on Neutrophils

A. Methods

The procedure used for detecting C5aR content on neutrophils (requiring <1 hr for final analysis) was as follows:

1. 100 µl whole blood from a mouse CLP model of sepsis (generated as described in the Example 2) was incubated with 1 µg of FITC-labeled anti-C5aR antibody (Research Diagnostics Inc, Flanders N.J.) for 30 min at room temperature.
2. The blood was incubated in a lysis buffer for 10 min.
3. The remaining leukocytes were spun down and re-suspended in 1% paraformaldehyde in phosphate buffered saline.
4. Fluorescence intensity (C5aR content) of cells was detected by Flow Cytometry. The cells were analyzed on a flow cytometer (Coulter Corp., Miami, Fla., USA) using 488 nm excitation and a 525-nm bandpass filter for FITC staining. Volts for FLI was set to 700, and Gain for Forward Scatter was set to 2. Granulocytes was gated according to side-scatter and forward-scatter detection.

B. Results

The present example demonstrates, using rats with CLP-induced sepsis and flow cytometry and antibody based detection methods, that surface expression of C5aR on blood neutrophils significantly fell, starting as early as 4 hours after the onset of CLP-induced sepsis, reached a nadir at 24 hours, and slowly increased thereafter (FIG. 1). The loss of C5aR on the neutrophil surface was apparently due to internalization of C5aR triggered by contact with C5a in the blood.

The ability of neutrophils from septic animals to respond chemotactically in vitro to C5a was depressed, inversely correlated with the number of C5aR on the surfaces of neutrophils (FIG. 2A). The data show that neutrophils with higher numbers of C5aR during sepsis are associated with enhanced survival of the animals, while the opposite is true with neutrophils that have low numbers of C5aR. Another functional parameter is the ability of neutrophils to generate reactive oxygen species (ROS), which are required for bacterial killing by neutrophils. In this study, a positive correlation was observed between the ability of neutrophils to produce ROS and higher C5aR levels on neutrophils (FIG. 2B). Taken together, the results establish a linkage between C5aR content on neutrophils and their functional ability (chemotactic responsiveness and H2O2 production), both of which represent protective mechanisms.

Figure 3:
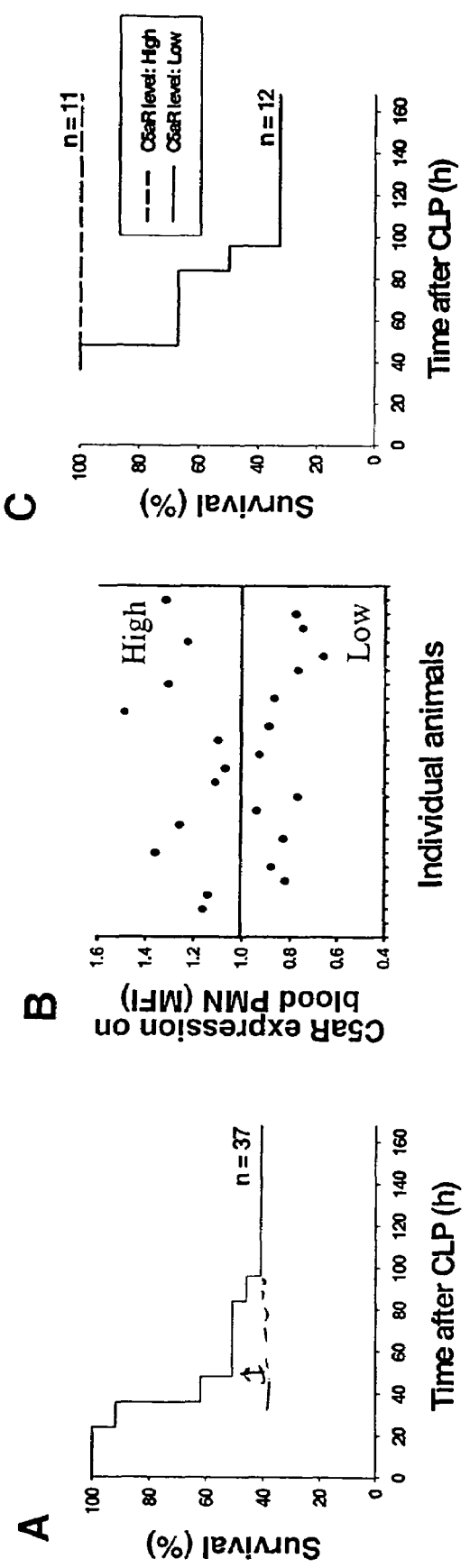
FIGS. 3A-3C show the correlation of C5aR expression on neutrophils with sepsis survival rates.

Levels of C5aR surface expression on neutrophils obtained 36 hours after CLP were positively correlated with the survival of individual animals after CLP (FIG. 3). All animals with C5aR levels higher than the overall median (1.0), as measured at 36 hours, survived, while animals with C5aR levels lower than the median showed a survival rate of only 33% within the next 3 days.

EXAMPLE 2

Blockage of C5aR

This Example describes the effect of blockage of the C5aR with an antibody on sepsis. To generate the mouse sepsis model (the CLP model), approximately ⅔ of the cecum was ligated through a 1.5 cm abdominal midline incision. The ligated part of the cecum was punctured through and through with a 21 gauge needle. After repositioning of the bowel, the abdomen was closed in layers, using a 4.0 surgical suture (Ethicon Inc., Somerville, N.J., USA) and metallic clips. An antagonist against C5aR (Woodruff et al., Inflammation 25, 171-7. (2001); Haynes et al., Biochem Pharmacol 60, 729-33. (2000); Strachan et al., J Immunol 164, 6560-5. (2000); Paczkowski et al., Br J Pharmacol 128, 1461-6. (1999); Finch et al., J Med Chem,42, 1965-74. (1999); Strachan et al., Br J Pharmacol 134, 1778-86. (2001); each of which was herein incorporated by reference) was injected intravenously (i.v.) at the indicated time point of CLP, using concentrations between 1-3 mg/kg body weight in 200 µl Dulbecco phosphate buffer solution (DPBS). Control animals were injected with 200 µl DPBS alone at the indicated time point of CLP.

Figure 4:
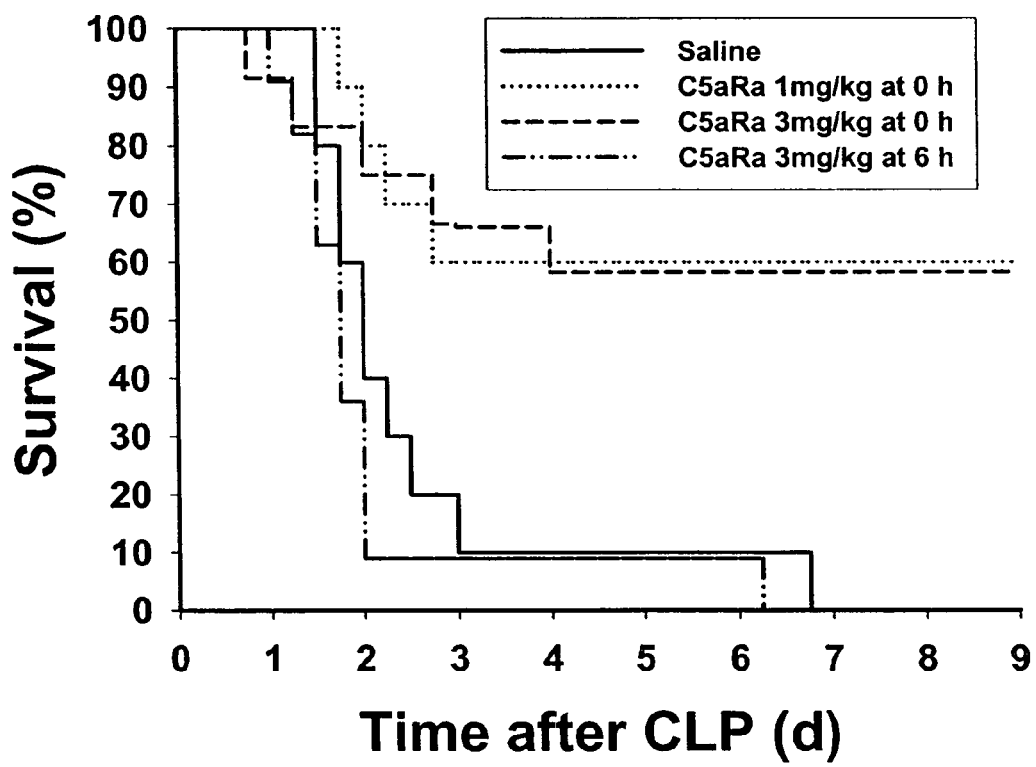
FIG. 4 shows the survival of CLP mice after treatment with a C5aRa antagonist.

Blockade of C5aR by this antagonist resulted in significantly improved survival as shown in FIG. 4, when compared to control animals. The activity of the C5aR antagonist was also confirmed in vitro by chemotaxis experiments, showing significantly reduced chemotactic responses of mouse neutrophils to mouse C5a when the cells were pre-incubated with the C5aR antagonist. In addition, blockade of C5aR by this antagonist resulted in significantly reduced lung injury in a model of immune complex induced lung injury as measured by leakage of $^{125}$I-labeled bovine serum albumin (BSA).

Figure 5:
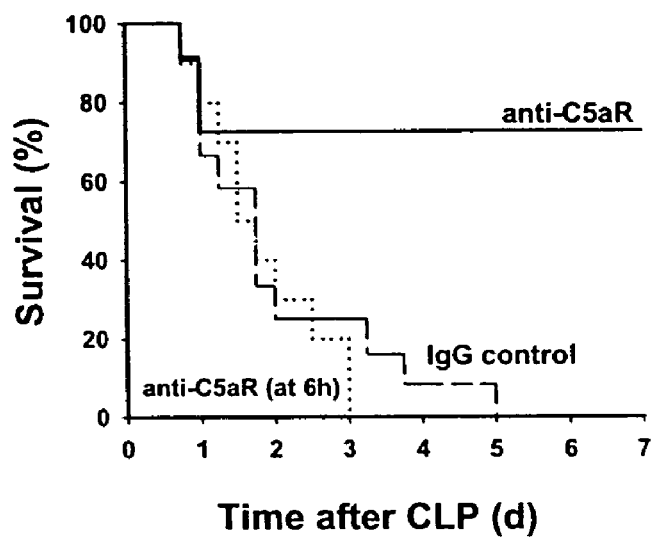
FIG. 5 shows the survival of CLP mice after treatment with an antibody to C5aRa.

An antibody to mouse C5aR (anti-C5aR) was used to demonstrate that C5aR expression is increased in lung, liver kidney and heart during the onset of CLP induced sepsis in mice. Binding of $^{125}$I-anti-C5aR to these organs was significantly increased during the onset of CLP-induced sepsis when compared to the binding of an irrelevant IgG antibody. 100 ng $^{125}$I-anti-C5aR and 2 µg unlabeled αC5aR in 200 µl DPBS were infused 15 minutes before sacrifice of mice 3, 6 and 12 hours after CLP. In addition, RNA was isolated from lung, liver, kidney and heart at 3, 6 and 12 hours after CLP and RT-PCR experiments were conducted. mRNA expression for C5aR was strongly increased during CLP induced sepsis in these organs but not in brain, thyroid or small intestine. Immunohistochemical staining of lung, liver, kidney and heart 12 hours after CLP in mice revealed patterns of enhanced C5aR expression in organs when compared to control organs. Finally, the effects of anti-C5aR treatment for the outcome of sepsis in mice were investigated. 20 µg anti-C5aR (per 30g mouse) in 200 µl DPBS were infused i.v. at the time of CLP induction. Control animals were infused with an equal amount of irrelevant IgG. The results of this experiment are shown in FIG. 5. In the group of animals injected with anti-C5aR, survival was significantly improved compared to the group of animals injected with irrelevant IgG. 77% of the anti-C5aR injected animals were survived 7 days after CLP while in the group treated with irrelevant IgG none of the animals survived beyond 5 days after CLP.

EXAMPLE 3

Protection of Innate Immunity by C5aR Antagonist

A. Materials and Methods

Reagents and chemicals

All materials were obtained from Sigma Chemical Co. (St. Louis, Mo.) unless otherwise indicated.

Cloning and Expression of mC5a

Total RNA was isolated from normal mouse liver tissue using the guanidine isothiocyanate method. The mC5a sequence was subcloned into pET 15b expression vector (Novagen, Madison, Wis.) using the primers 5'-GTG TCG CGA GTC AGC <u>CATATG</u> AAC CTG CAT CTC CTA-3' (SEQ ID NO:1; sense, NdeI site underlined) and 5'-GTC ACA TCG CGA CAC <u>GGATCC</u> TCA CCT TCC CAG TTG GAC-3' (SEQ ID NO:2; antisense, BamHI site underlined). After expression of mouse C5a in BL21 (DE3) pLysS cells (Novagen, Madison, Wis.), the recombinant protein was purified over a Ni$^{2+}$ column and used for subsequent experiments. mC5a had biological (chemotactic) activity and demonstrated high-affinity binding to mouse neutrophils.

Synthesis and Purification of C5aRa F[OPdChaWR]

Synthesis of the linear hexapeptide F[OPdChaWR] was done as described previously (Short et al., (1999) *Br. J. Pharmacol.* 126,551-554), followed by cyclization involving the side chain of ornithine and carboxyl-terminal arginine (Finch et al., (1999) *J. Med. Chem.* 42,1965-1974). The peptide was purified using preparative reversed-phase HPLC. Eluted fractions were characterized by mass spectrometry (matrix-assisted laser desorption ionization). The efficacy of the cyclic hexapeptide F[OPdChaWR] was characterized in vivo and in vitro, as described below.

Models of Inflammation

Cecal Ligation Puncture-Induced Sepsis

Male specific pathogen-free B 10.D2/nSnJ mice (6 to 8 wk of age weighing 25-30 g; Jackson Laboratories, Bar Harbor, Me.) were used in all experiments. Mice were anesthetized with ketamine i.p. (20 mg/100 g body weight). A 1 cm-long midline incision was made to expose the cecum and adjoining intestine. With a 4-0 silk suture, the cecum was tightly ligated below the ileocecal valve without causing bowel obstruction. The cecum was punctured through and through with a 21 gauge needle and gently squeezed to extrude luminal contents, ensuring patency of the two puncture holes. The abdominal incision was then closed with a 4-0 nylon suture and skin metallic clips (Ethicon, Somerville, N.Y.). Sham-operated animals underwent the same procedure except for ligation and puncture of the cecum. Immediately thereafter, CLP mice received either 200 µL of saline alone or C5aRa in 200 µL saline i.v. (at a final concentration of 1-3 mg/kg body weight). In one experiment, i.v. infusion of C5aRa was delayed for 6 h. Before and after surgery, mice had unrestricted access to food and water. Survival rates were determined over a 9 day period, with assessment every 6 h.

IgG Immune Complex-Induced Lung Injury

Male specific pathogen-free B 10.D2/nSnJ mice were anesthetized i.p. with ketamine (20 mg/100 g body weight). To induce acute inflammatory lung injury, mice were intratracheally instilled with 250 μg antibody to bovine serum albumin (anti-BSA; ICN Biomedicals, Costa Mesa, Calif.) in a volume of 40 μL DPBS (Gibco BRL, Grand Island, N.Y.), followed by i.v. injection of 500 μg BSA (<1 ng endotoxin/mg) in 200 μL DPBS. Some animals received C5aRa (1 mg/kg body weight) intratracheally together with the anti-BSA. Negative control animals were subjected to intratracheal instillation of 40 μL DPBS alone. For analysis of pulmonary vascular permeability, trace amounts of $^{125}$I-labeled BSA were injected i.v. Four hours after IgG immune complex deposition, mice were killed, the pulmonary circulation flushed with 1 mL DPBS by pulmonary artery injection, and the lungs surgically removed. The extent of lung injury was quantified by calculating the lung permeability index, determined by comparing the amount of $^{125}$I-BSA present in lung parenchyma to the amount present in 100 μL blood obtained from the inferior vena cava at the time of death.

Isolation of Mouse Peritoneal Neutrophils

Mice were injected i.p. with 2.5 mL sterile 3% thioglycolate medium (DIFCO Laboratories, Detroit, Mich.) for harvesting of mouse neutrophils (Ajuebor et al., (1999) *J. Immunol.* 162,1685-1691). Five hours later, mice were killed and the peritoneal cavity was lavaged four times with 10 mL DPBS. Fluids were centrifuged and residual red blood cells removed by a hypotonic lysis step. Remaining peritoneal cells were washed and resuspended in HBSS. Aliquots of cells were stained with Diff-Quik Stain (Dade International, Miami, Fla.) and examined for neutrophil purity (>95%) and viability (>97%) by trypan blue exclusion (Fildes et al., (1998) *J. Trauma* 45,479-484).

Radiolabeling and Binding Assays

For binding studies, mC5a was labeled with 125, using the chloramine T-based protocol (Bennett et al., (1997) *Methods Enzymol.* 288,134-148) with gentle oxidation, which preserves chemotactic activity of mC5a for mouse neutrophils. Isolated neutrophils were incubated for 1 h at 4° C. in binding buffer (HBSS without $Ca^{2+}$ and containing 1% BSA) to block nonspecific surface binding sites. After gentle washing, neutrophils ($2 \times 10^6$ cells) were incubated at 4° C. in binding buffer (HBSS with $Ca^{2+}$ containing 0.1% BSA) (in a final volume of 200 μL) with 100 pM $^{125}$I-mC5a (specific activity 23.5 μCi/μg) in the absence or presence of increasing amounts of either unlabeled mC5a or C5aRa (ranging from $10^{-12}$ to $10^{-4}$ M). After an incubation interval of 20 min at 4° C., cell suspensions were layered over 20% sucrose and sedimented by centrifugation at 11,000 g (Beckman Microfuge B, Palo Alto, Calif.) for 2 min. The tubes were then frozen at –80° C. and the tips containing the cell pellet were cut off to determine the cell-bound $^{125}$I-mC5a, using a gamma counter (1261 Multigamma, EG & G Wallac, Co., Gaithersburg, Md.). Binding affinities ($K_d$ values) of C5a were calculated in the conventional manner (Chenoweth et al., (1978) *Proc. Natl. Acad. Sci. USA* 75,3943-3947). In another set of experiments, C5aRa was labeled with $^{125}$I by the chloramine T method, taking advantage of the electrophilic aromatic region of phenylalanine (Sharma et al., (1991) *J. Org. Chem.* 56,4981-4983). The integrity of 12.5I-C5aRa after the labeling procedure was confirmed in vitro by chemotaxis assays (see below). Using peritoneal mouse neutrophils, competitive binding studies using 100 pM 1$^{25}$, —C5aRa (specific activity 33.9 μCi/μg) with increasing amounts of unlabeled C5aRa or mC5a were performed as described above.

Chemotaxis Assay

After neutrophil isolation, cells were fluorescein-labeled with BCECF (2',7'-bis [2-carboxyethyl]-5-[and 6]-carboxyfluorescein acetoxymethyl ester) (Molecular Probes, Eugene, Oreg.). Labeled neutrophils ($5 \times 10^6$ cells/mL) were then loaded into the upper chambers of 96-well minichambers (NeuroProbe, Cabin John, Md.). Lower chambers were loaded with increasing amounts of mC5a in the presence or absence of different concentrations of C5aRa, ranging from 0.1 nM-10 μM. The upper and lower chambers were separated by a polycarbonate membrane of 3 μm porosity. Minichambers were incubated for 60 min at 37° C. The number of cells migrating through polycarbonate filters to the lower surface was measured by cytofluorometry (Cytofluor II, Perseptive Biosystems, Framingham, Mass.). For each measurement, quadruplicate samples were used.

Measurement of Neutrophil Oxidative Burst $H_2O_2$ generation was determined in the presence of 1 mM sodium azide. As indicated, mouse neutrophils ($2 \times 10^6$ cells/mL) were pretreated with mC5a (10 nM) for 60 min at 37° C. in the presence or absence of different amounts of C5aRa. To stimulate neutrophils, cells were then incubated with PMA (25 ng/mL) for an additional 10 min. The reaction was stopped by addition of 0.1 mL trichloroacetic acid (50% v/v), then ferrous ammonium sulfate (1.5 mM) and potassium thiocyanate (0.25 M) were added to supernatant fluids. The absorbance of the ferrithiocyanate complex was measured at 480 nm and compared with a standard curve generated from dilutions of reference solutions of $H_2O_2$.

Clearance Studies

To evaluate the blood clearance of C5aRa, anesthetized mice were injected i.v. with C5aRa (1 mg/kg body weight) in 200 μL DPBS containing trace amounts of $1^{25}$I-C5aRa (specific activity 33.9 μCi/μg). Sixty seconds after administration, 5 μL blood was drawn from a small incision at the tail tip, followed by direct pressure to stop further bleeding. Animals were killed after specified periods (1, 2, 3, 6, 12, 24, 36, 48, 72, 96 h) and the radioactivity of blood samples (100 μL aliquots) was measured in a gamma counter (1261 Multigamma, EG&G, Wallac, Gaithersburg, Md.) and compared with the value obtained 1.0 min after infusion of C5aRa.

Statistical Analyses

All values were expressed as mean±SE. Results were considered statistically significant where P<0.05. For analysis of survival curves, log rank and –2 log rank tests were used. Outcomes in different treatment groups were compared using $\chi^2$ and Fisher's exact tests. Data sets of binding, chemotaxis and oxidative burst assays were analyzed with one-way ANOVA; differences in the mean values among experimental groups were then compared using the Tukey multiple comparison test.

B. Results

Ability of C5aRa to Reduce Binding of mC5a to Mouse Peritoneal Neutrophils

Figure 6:
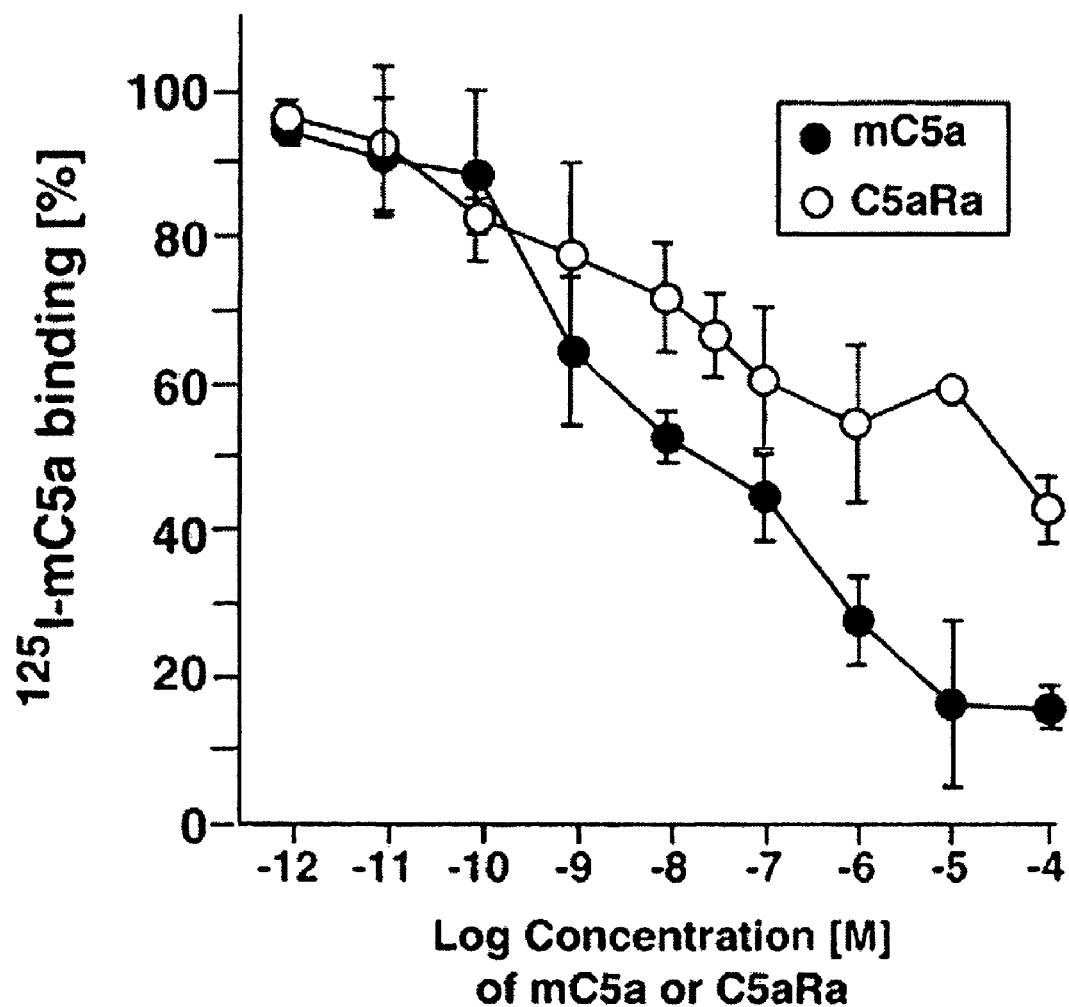

Recent reports have described CSaRa binding affinities to rat and human neutrophils (Wong et al., (1998) *J. Med. Chem.* 41,3417-3425; Short et al., (1999) *Br. J. Pharmacol.* 128,511-514). To assess whether C5aRa also binds to mouse neutrophils, competitive binding studies using C5aRa and mC5a were undertaken. Mouse neutrophils (isolated from peritoneal exudates) were incubated for 20 min at 4° C. with 100 pM $^{125}$I-mC5a in the presence of increasing doses of either unlabeled mC5a or C5aRa. As shown in FIG. 6 (filled circles), mC5a demonstrated dose-dependent competitive binding, with a calculated $K_d$ of ~3 nM. C5aRa (open circles) also demonstrated significant competitive binding with a calculated Kd of ~30 nM. These experiments indicate that C5aRa inhibits the binding of mC5a to mouse neutrophils.

Blocking by C5aRa of Mouse Neutrophil Chemotactic Responses to mC5a

Figure 7:
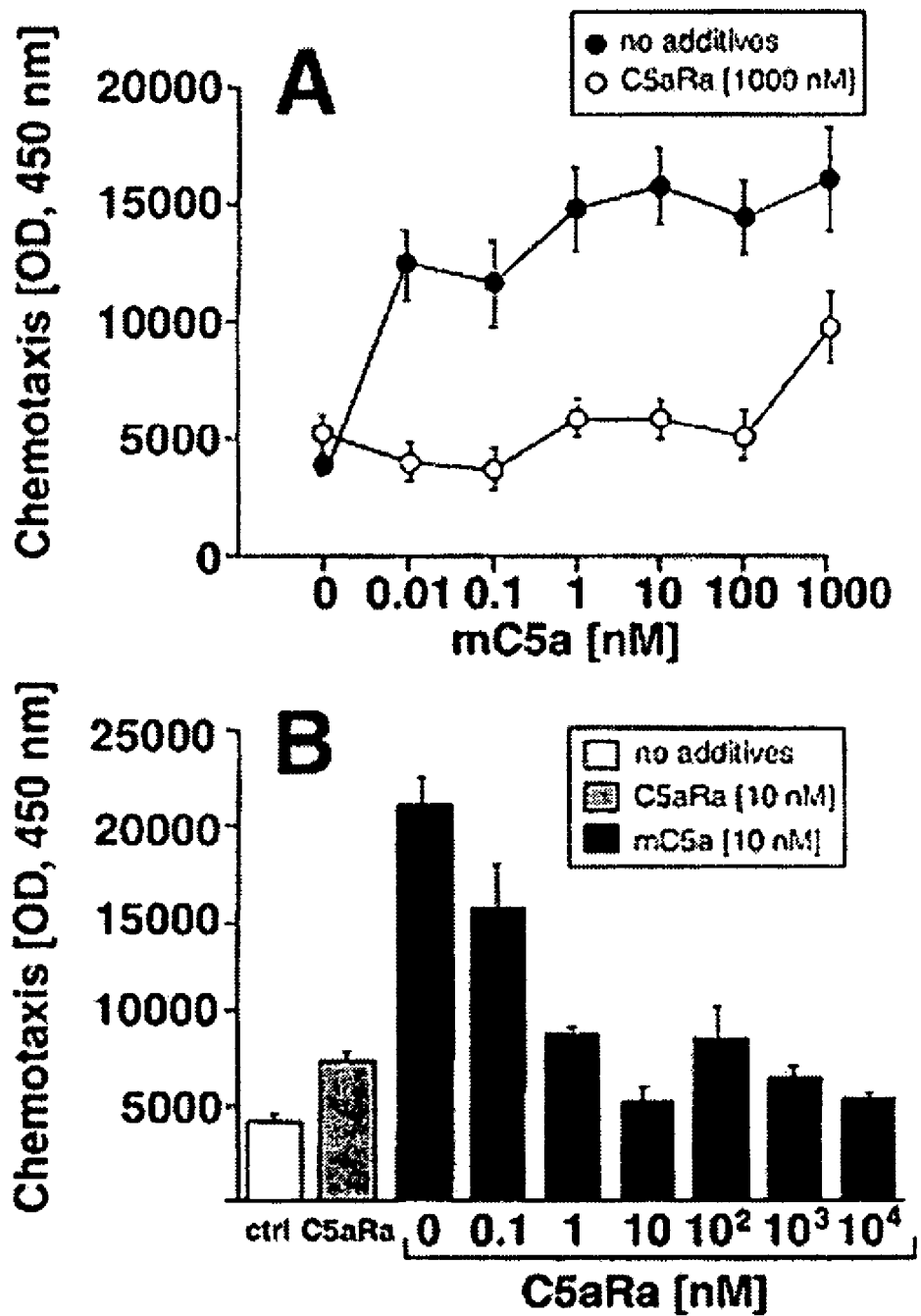

To assess in vitro the effects of C5aRa on migrational responses of mouse neutrophils to mC5a, chemotactic responses in the absence or presence of a dose range of C5aRa were determined. When mouseneutrophils were exposed to mC5a (0.01-1000 nM), a typical dose-dependent chemotactic response was found, reaching a plateau between 1 and 10 nM mC5a (FIG. 7A, filled circles). In the presence of 1000 nM C5aRa, the chemotactic response of mouse neutrophils was almost completely suppressed over a wide dose range (0.01-100 nM) of mC5a.

In a second set of experiments, the chemotactic responses of mouse neutrophils to a constant dose (10 nM) of mC5a in the presence of increasing C5aRa concentrations (0.1 nM-10 µM) were assessed (FIG. 7B). The presence of 10 nM C5aRa alone evoked a very weak chemotactic response, if at all (graybar). 10 nM mC5a in the absence of C5aRa evoked a robust chemotactic response of neutrophils (first black bar). In contrast, a dose-dependent inhibition of neutrophil response to mC5a was observed in the copresence of $0.1\text{-}10^4$ nM C5aRa. In this assay the calculated IC50 for C5aRa was ~0.5 nM. These data indicate a dose-dependent inhibition by C5aRa of chemotactic responses by mouse neutrophils to mC5a.

Reversal by C5aRa of C5a-Induced Defect in the Oxidative Burst of Neutrophils

Figure 8:
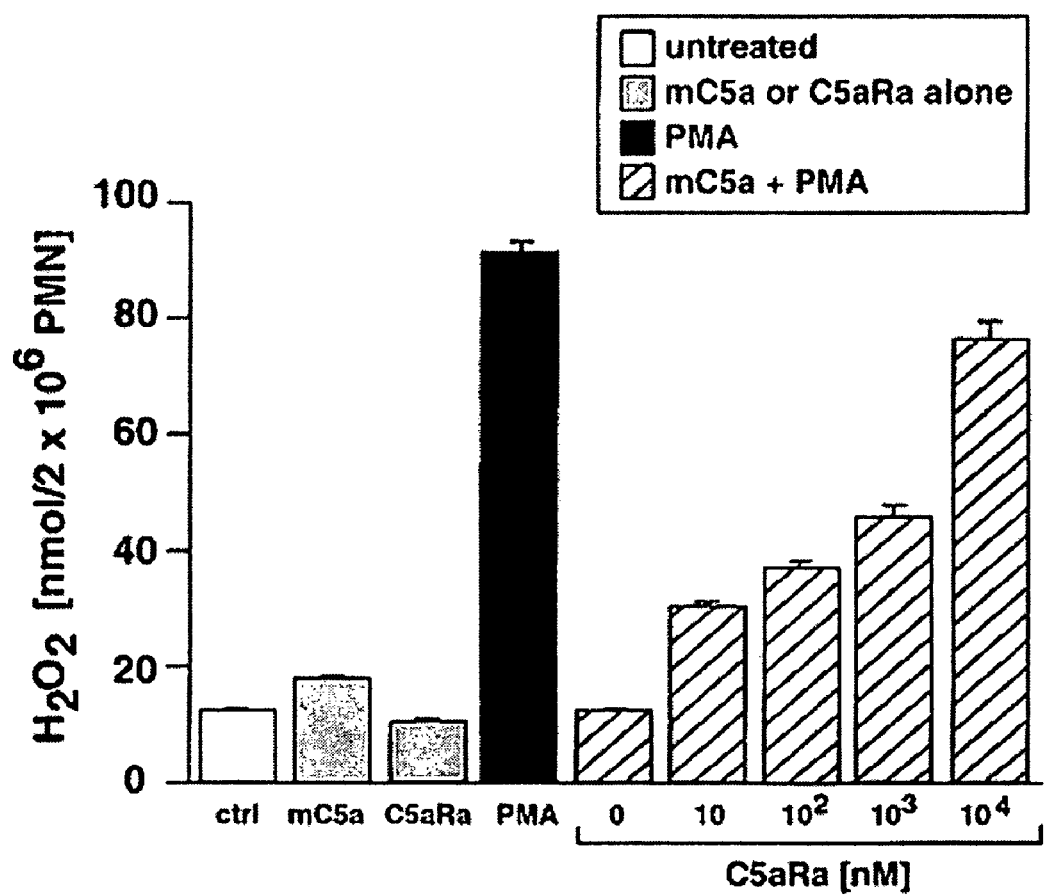
FIG. 8 shows the In vitro effects of C5aRa on reversal of C5a-induced defective $H_2O_2$ responses of mouse neutrophils stimulated with PMA (25 ng/mL).

During sepsis, plasma levels of C5a are increased (Goya et al., (1994) *Surgery* 115,145-155; Hecke et al., (1997) *Crit. Care Med.* 25,2015-2024) and suppression of the neutrophil oxidative burst (production of $O_2$. and $H_2O_2$) occurs, resulting in impaired bacterial killing (Czermak et al., (1999) *Nature Med.* 5,788-792; Koch et al., (1997) *Shock* 7,42-48). In CLP-induced sepsis in rats, the $H_2O_2$ response of blood neutrophils is defective (Czermak et al., supra). In vitro exposure of neutrophils to C5a reproduces the defect in the oxidative response found in blood neutrophils during sepsis (Czermak et al., supra). In this example, the effects of C5aRa on the C5a-induced loss of the oxidative response in neutrophils were investigated. Mouse neutrophils were exposed to buffer (ctrl), to 10 nM mC5a alone, or to 10 nM C5aRa alone for 60 min at 37° C., followed by addition (where indicated) of PMA (25 ng/mL for 10 min at 37° C.). The $H_2O_2$ response was then measured. As shown in FIG. 8, neither mC5a alone nor C5aRa alone significantly altered basal $H_2O_2$ production in neutrophils when compared with ctrl cells (white bar and first two light gray bars). Addition of PMA to neutrophils otherwise untreated caused a large increase in $H_2O_2$ generation (black bar). In mC5a-exposedneutrophils (in the absence of C5aRa), followed by stimulationwith PMA, production of $H_2O_2$ was completely abolished (first cross-hatched bar). The copresence of 10 nM mC5a with increasing concentrations of C5aRa (10 nM-10 µM) with neutrophils for 60 min at 37° C. led to a progressive and significant restoration of $H_2O_2$ generation (second to fifth cross-hatched bars). Thus, C5a-induced impairment of the oxidative response in activated neutrophils could be reversed by the presence of C5aRa in a dose-dependent manner. These data parallel the efficacy of C5aRa in blockade of C5a-dependent neutrophil chemotactic activity (FIG. 7B).

C5aRa Clearance in Mouse Blood

Figure 9:
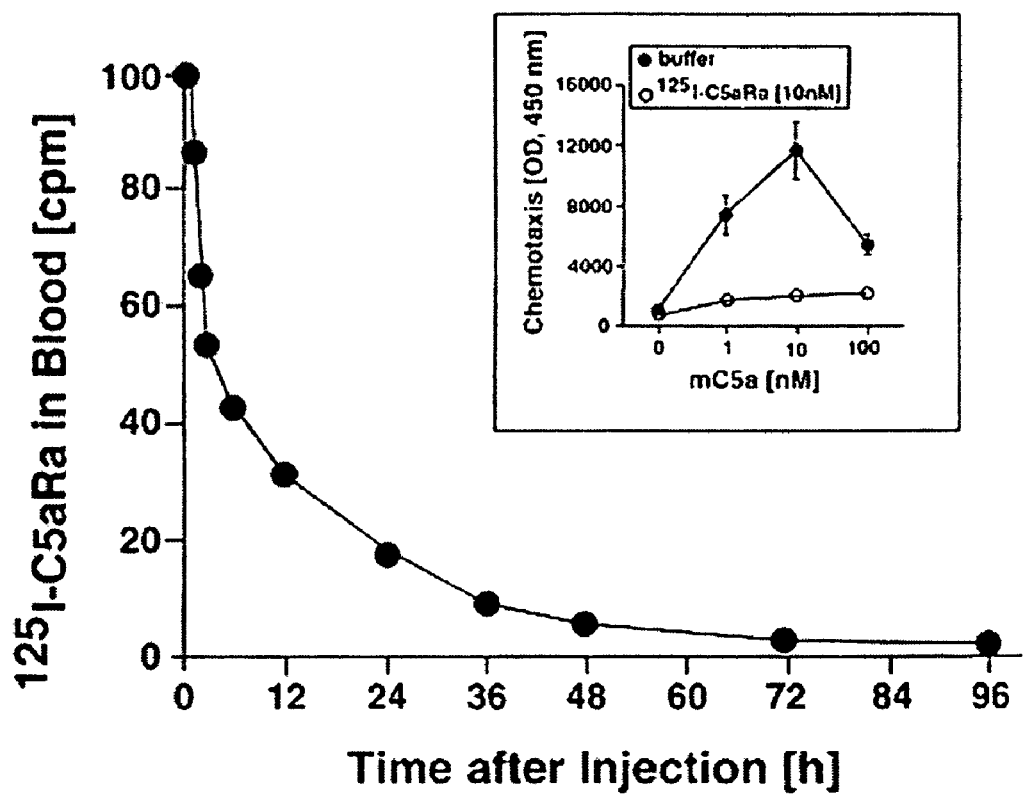
FIG. 9 shows blood clearance of $^{125}$I-C5aRa in mice. After $^{125}$I-labeling of C5aRa, its functional activity was determined in chemotaxis assays using increasing amounts of mC5a in the presence of 10 nM $^{125}$I-C5aRa (inset). Semilogarithmic plots of blood clearance curve of $^{125}$I-C5aRa were normalized to the 1.0 min time point. Data are expressed as percent of blood values obtained immediately after i.v. injection of $^{125}$I-C5aRa. Mean±SE of 5 animals at each time point.

To determine whether treatment of CLP mice with C5aRa would improve survival rates, the in vivo bloodclearance of C5aRa was first assessed. C5aRa was $^{125}$I-labeled before i.v. administration into mice. To ensure the functional integrity of C5aRa after the labeling procedure, chemotaxis assays were performed using $^{125}$I-C5aRa (10 nM) in the presence of mC5a (1-100 nM). Mouse neutrophils were exposed to a range of concentrations of mC5a in the absence or presence of 10 nM $^{125}$I-C5aRa, similar to the protocol in FIG. 7B. As shown in FIG. 9 (inset), radiolabeled C5aRa virtually completely suppressed the chemotactic response to all doses of mC5a (open circles), indicating intact biological activity of $^{125}$I-C5aRa. The blood clearance of C5aRa in mice after a single i.v. bolus of 1 mg/kg C5aRa with trace amounts of $^{125}$I-labeled C5aRa was determined. As shown in FIG. 9, a multiphasic decline in whole blood concentrations was observed. The early, rapid clearance phase (<3 h) was characterized by a mean half-life of ~4 h, whereas the later phase (24-72 h) demonstrated a mean half-life of ~12 h. The slower clearance phase accounted for an average of 63% of the total area for the blood concentration vs. time; 36 h after C5aRa application, the C5aRa concentration reached 10% of the initial dose in blood.

Ability of C5aRa to Diminish C5a-Dependent Inflammatory Lung Injury in Mice

Figure 10:
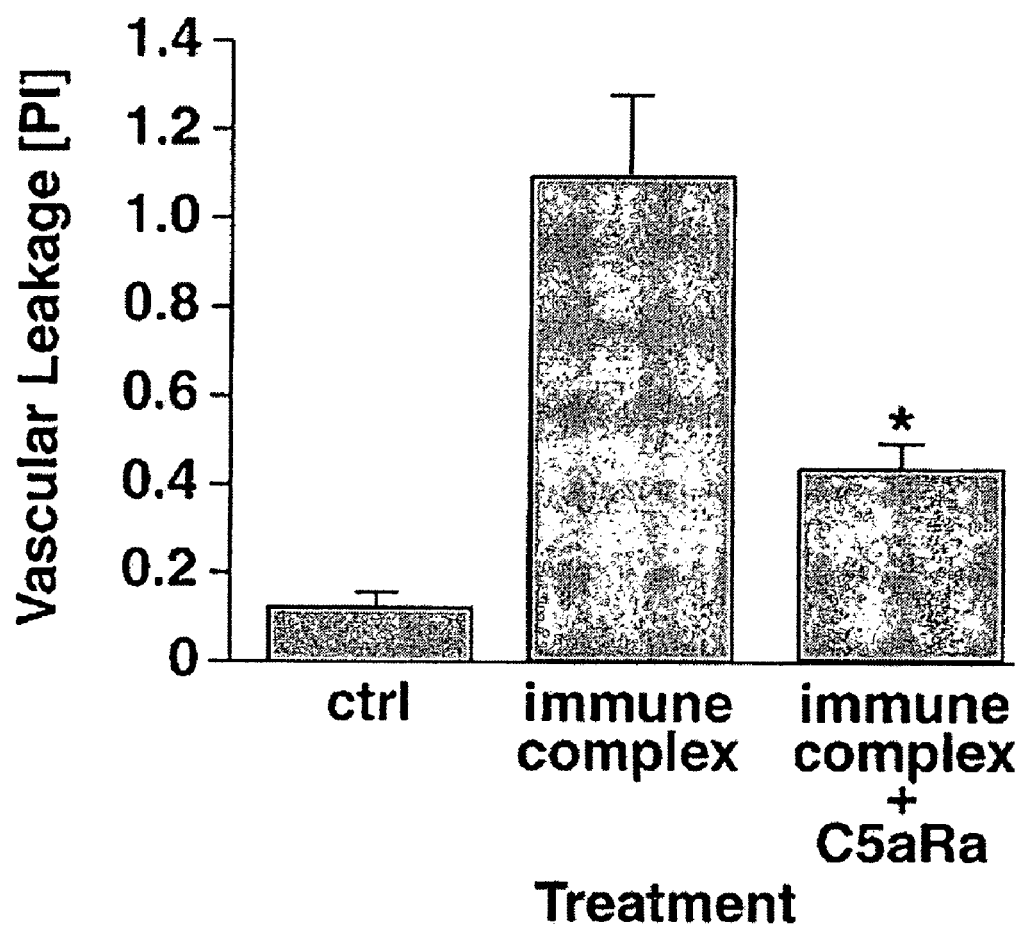
FIG. 10 shows the effects of C5aRa (1 mg/kg body weight administered intratracheally) on acute inflammatory injury of mouse lungs after intrapulmonary deposition of IgG immune complexes.
Figure 11:
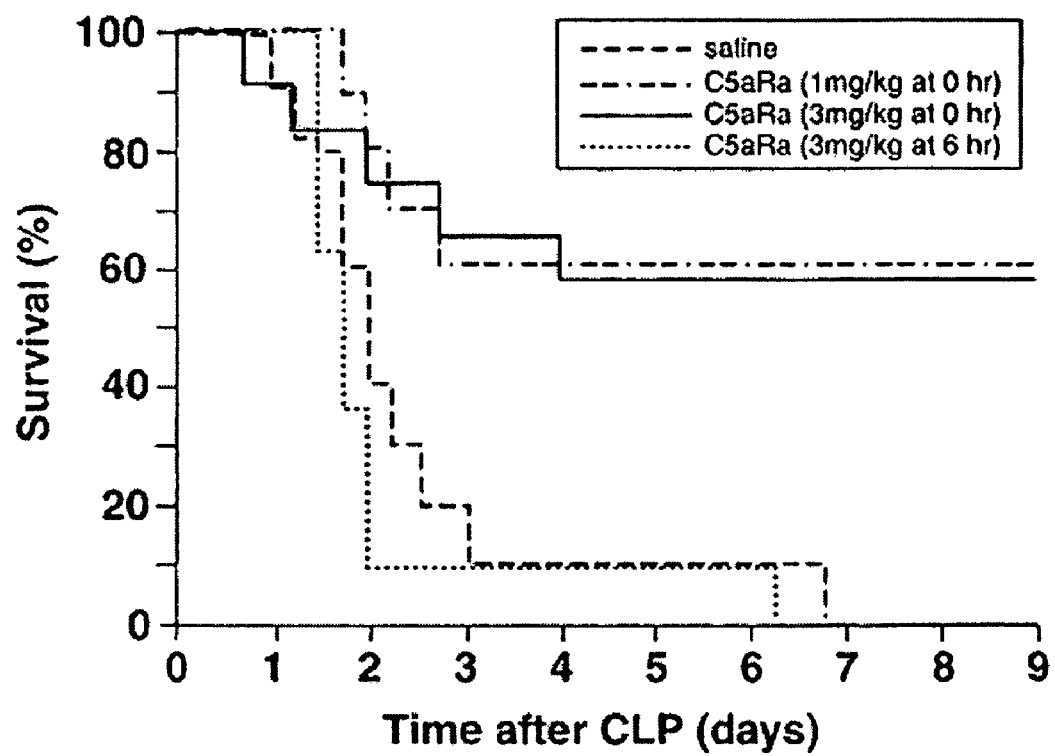
FIG. 11 shows survival curves of mice after CLP as a function of i.v. treatment with either 200 µL saline alone or C5aRa (1-3 mg/kg body weight) in 200 µL saline.

Lung inflammatory injury induced by intrapulmonary deposition of IgG immune complex is C5 and C5a dependent (Larsen et al., (1981) *Am. Rev. Respir. Dis.* 123,434-439; Mulligan et al., (1996) *J. Clin. Invest.* 98,503-512). In the case of C5a, the bulk of C5a generated appears to be within the distal airway compartment (Mulligan et al., supra). In preliminary experiments, it was determined that the intratracheal instillation of 250 µg anti-BSA with an i.v. infusion of 500 µg BSA would induce acute inflammatory injury in mouse lung at 4 h. Accordingly, these conditions were used in the mouse model of acute lung injury. To determine lung vascular leakage 4 h after immune complex deposition, extravasation of i.v. administered $^{125}$I-labeled BSA into lungs was measured. Control mice, which received 40 µL sterile saline intratracheally, exhibited a vascular permeability index of 0.13±0.02 (FIG. 10). This index rose nearly ninefold in mice with immune complex-induced alveolitis. However, the presence of C5aRa (1 mg/kg body weight given intratracheally at time 0) resulted in a substantial reduction in the permeability index (immune complex ±C5aRa) vs. the positive control group of immune complexes alone. The C5aRa-treated group showed a significant reduction (~70%, P<0.05) in the permeability index. Higher doses of C5aRa (up to 10 mg/kg) did not further reduce the permeability index. Thus, in animals receiving a direct intrapulmonary insult after deposition of IgG immune complexes, airway presence of C5aRa caused significantly reduced lung vascular leakage.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

We claim:

1. A method of treating sepsis in a subject suffering from sepsis, wherein said sepsis is selected from the group consisting of sepsis due to gram-positive bacteremia and sepsis due to gram-negative bacteremia comprising
   (a) providing a reagent capable of blocking C5a receptor, wherein said reagent is a monoclonal antibody that specifically binds to said C5a receptor; and
   (b) administering said reagent to said subject, wherein said subject's survival is prolonged.

2. The method of claim 1, wherein said administering results in a decrease in symptoms of sepsis in the subject.

* * * * *